US009278173B2

(12) United States Patent
Mejlhede et al.

(10) Patent No.: US 9,278,173 B2
(45) Date of Patent: Mar. 8, 2016

(54) DEVICE FOR ADMINISTRATION

(75) Inventors: Signe Thorning Mejlhede, Svinninge (DK); Lasse W. Mogensen, Søborg (DK); Steffen Gyrn, Ringsted (DK); Elo Hørdum, Hørsholm (DK)

(73) Assignee: UNOMEDICAL A/S, Birkeroed (DK)

( * ) Notice: Subject to any disclaimer, the term of this patent is extended or adjusted under 35 U.S.C. 154(b) by 204 days.

(21) Appl. No.: 12/158,520

(22) PCT Filed: Dec. 22, 2006

(86) PCT No.: PCT/DK2006/000737
§ 371 (c)(1),
(2), (4) Date: Nov. 26, 2008

(87) PCT Pub. No.: WO2007/071255
PCT Pub. Date: Jun. 28, 2007

(65) Prior Publication Data
US 2009/0076453 A1 Mar. 19, 2009

Related U.S. Application Data

(60) Provisional application No. 60/753,684, filed on Dec. 23, 2005, provisional application No. 60/762,231, filed on Jan. 25, 2006, provisional application No. 60/816,767, filed on Jun. 27, 2006.

(30) Foreign Application Priority Data

Jan. 24, 2006 (DK) ................................. 2006 00103

(51) Int. Cl.
*A61M 5/142* (2006.01)
*A61M 5/158* (2006.01)
*A61M 39/12* (2006.01)

(52) U.S. Cl.
CPC ........... *A61M 5/14248* (2013.01); *A61M 5/142* (2013.01); *A61M 5/158* (2013.01);
(Continued)

(58) Field of Classification Search
CPC .......... A61M 5/14248; A61M 5/2033; A61M 31/002; A61M 2005/14268; A61M 2005/14252

USPC .............................................. 604/890.1, 151
See application file for complete search history.

(56) References Cited

U.S. PATENT DOCUMENTS

| 1,592,462 A | 6/1926 | MacGregor |
| 2,047,010 A | 6/1936 | Dickinson |

(Continued)

FOREIGN PATENT DOCUMENTS

| DE | 4 342 329 A1 | 6/1994 |
| DE | 196 31 921 A1 | 3/1997 |

(Continued)

OTHER PUBLICATIONS

"Why inset®?" inset® infusion set product overview; http://web.archive.org/web/20040906102448/http://www.infusion-set.com/Default.asp?ID=108; two pages.

(Continued)

*Primary Examiner* — Nathan R Price
*Assistant Examiner* — Weng Lee
(74) *Attorney, Agent, or Firm* — Wilson Sonsini Goodrich & Rosati

(57) ABSTRACT

The application relates to a device for an intermittent or continuous administration of a therapeutical substance, such as insulin, comprising an injection part and a fluid delivery part (3,4). The fluid delivery part normally comprises a reservoir (4), transferal means e.g. in form of a pump and a house (3), and the injection part normally comprises a base plate (10), a cannula part (1,16) comprising a cannula (9) extending past the proximal side of the base plate and means for fixation of the base plate to the skin of the user. According to the application the device comprises a base plate (10), a cannula part (1, 1b) comprising a body providing a through-going opening leading liquid to a cannula (9) which cannula (9) extends past the proximal side of the base plate (10) and means (21) for fixation of the base plate to the skin of the user wherein a flexible part is arranged in an area between the subcutaneously positioned section of the cannula (9) and the fluid delivery part (3, 4).

24 Claims, 27 Drawing Sheets

(52) U.S. Cl.
CPC .... *A61M 39/12* (2013.01); *A61M 2005/14252* (2013.01); *A61M 2005/14268* (2013.01); *A61M 2005/1581* (2013.01); *A61M 2005/1587* (2013.01)

(56) References Cited

U.S. PATENT DOCUMENTS

| | | |
|---|---|---|
| 2,295,849 A | 9/1942 | Kayden |
| 2,690,529 A | 9/1954 | Lindblad |
| 2,972,779 A | 2/1961 | Cowley |
| 3,059,802 A | 10/1962 | Mitchell |
| 3,074,541 A | 1/1963 | Roehr |
| 3,149,186 A | 9/1964 | Coanda |
| 3,221,739 A | 12/1965 | Rosenthal |
| 3,221,740 A | 12/1965 | Rosenthal |
| 3,306,291 A | 2/1967 | Burke |
| 3,485,352 A | 12/1969 | Pilger |
| 3,509,879 A | 5/1970 | Bathish et al. |
| 3,519,158 A | 7/1970 | Anderson |
| 3,547,119 A | 12/1970 | Hall et al. |
| 3,575,337 A | 4/1971 | Bernhardt |
| 3,610,240 A | 10/1971 | Harautuneian |
| 3,615,039 A | 10/1971 | Ward |
| 3,670,727 A | 6/1972 | Reiterman |
| 3,783,895 A | 1/1974 | Weichselbaum |
| 3,788,374 A | 1/1974 | Saijo |
| 3,810,469 A | 5/1974 | Hurschman |
| 3,835,862 A | 9/1974 | Villari |
| 3,840,011 A | 10/1974 | Wright |
| 3,893,448 A | 7/1975 | Brantigan |
| 3,937,219 A | 2/1976 | Karakashian |
| 3,986,507 A | 10/1976 | Watt |
| 3,986,508 A | 10/1976 | Barrington |
| 3,995,518 A | 12/1976 | Spiroff |
| 4,022,205 A | 5/1977 | Tenczar |
| 4,188,950 A | 2/1980 | Wardlaw |
| 4,201,406 A | 5/1980 | Dennehey et al. |
| 4,227,528 A | 10/1980 | Wardlaw |
| 4,259,276 A | 3/1981 | Rawlings |
| 4,267,836 A | 5/1981 | Whitney et al. |
| 4,296,786 A | 10/1981 | Brignola |
| 4,315,505 A | 2/1982 | Crandall et al. |
| 4,333,455 A | 6/1982 | Bodicky |
| 4,334,551 A | 6/1982 | Pfister |
| D267,199 S | 12/1982 | Koenig |
| 4,378,015 A | 3/1983 | Wardlaw |
| 4,402,407 A | 9/1983 | Maly |
| 4,415,393 A | 11/1983 | Grimes |
| 4,417,886 A | 11/1983 | Frankhouser et al. |
| 4,464,178 A | 8/1984 | Dalton |
| 4,473,369 A | 9/1984 | Lueders et al. |
| 4,484,910 A | 11/1984 | Sarnoff et al. |
| 4,500,312 A | 2/1985 | McFarlane |
| 4,508,367 A | 4/1985 | Oreopoulos et al. |
| 4,525,157 A | 6/1985 | Vaillancourt |
| 4,530,695 A | 7/1985 | Phillips et al. |
| 4,531,937 A | 7/1985 | Yates |
| 4,543,088 A * | 9/1985 | Bootman et al. ......... 604/288.02 |
| 4,563,177 A | 1/1986 | Kamen |
| 4,610,469 A | 9/1986 | Wolff-Mooij |
| 4,617,019 A | 10/1986 | Fecht |
| 4,713,059 A | 12/1987 | Bickelhaupt et al. |
| 4,734,092 A | 3/1988 | Millerd |
| 4,755,173 A | 7/1988 | Konopka et al. |
| 4,817,603 A | 4/1989 | Turner et al. |
| RE32,922 E | 5/1989 | Levin et al. |
| 4,838,871 A | 6/1989 | Luther |
| 4,840,613 A | 6/1989 | Balbierz |
| 4,850,974 A | 7/1989 | Bickelhaupt et al. |
| 4,850,996 A | 7/1989 | Cree |
| 4,863,016 A | 9/1989 | Fong et al. |
| 4,878,897 A | 11/1989 | Katzin |
| 4,890,608 A | 1/1990 | Steer |
| 4,894,054 A | 1/1990 | Miskinyar |
| 4,895,570 A | 1/1990 | Larkin |
| 4,917,669 A | 4/1990 | Bonaldo |
| 4,935,010 A | 6/1990 | Cox et al. |
| 4,950,163 A | 8/1990 | Zimble |
| 4,950,252 A | 8/1990 | Luther et al. |
| 4,956,989 A | 9/1990 | Nakajima |
| 4,970,954 A | 11/1990 | Weir et al. |
| 4,978,338 A | 12/1990 | Melsky et al. |
| 4,982,842 A | 1/1991 | Hollister |
| 4,986,817 A | 1/1991 | Code |
| 4,994,042 A | 2/1991 | Vadher |
| 4,994,045 A | 2/1991 | Ranford |
| 5,011,475 A | 4/1991 | Olsen |
| 5,020,665 A | 6/1991 | Bruno |
| 5,024,662 A | 6/1991 | Menes et al. |
| 5,067,496 A | 11/1991 | Eisele |
| 5,092,853 A | 3/1992 | Couvertier, II |
| 5,098,389 A | 3/1992 | Cappucci |
| 5,112,313 A | 5/1992 | Sallee |
| 5,116,319 A | 5/1992 | Van den Haak |
| 5,116,325 A | 5/1992 | Paterson |
| 5,121,751 A | 6/1992 | Panalletta |
| 5,129,884 A | 7/1992 | Dysarz |
| 5,135,502 A | 8/1992 | Koenig, Jr. et al. |
| 5,137,516 A | 8/1992 | Rand et al. |
| 5,137,524 A | 8/1992 | Lynn et al. |
| 5,141,496 A | 8/1992 | Dalto et al. |
| 5,147,375 A | 9/1992 | Sullivan et al. |
| 5,163,915 A | 11/1992 | Holleron |
| 5,172,808 A | 12/1992 | Bruno |
| 5,176,643 A | 1/1993 | Kramer et al. |
| 5,176,650 A | 1/1993 | Haining |
| 5,176,662 A | 1/1993 | Bartholomew et al. |
| 5,186,712 A | 2/1993 | Kelso et al. |
| 5,188,611 A | 2/1993 | Orgain |
| RE34,223 E | 4/1993 | Bonaldo |
| 5,205,820 A | 4/1993 | Kriesel |
| 5,222,947 A | 6/1993 | D'Amico |
| 5,232,454 A | 8/1993 | Hollister |
| 5,248,301 A | 9/1993 | Koenig et al. |
| 5,256,149 A | 10/1993 | Banik et al. |
| 5,256,152 A | 10/1993 | Marks |
| 5,257,980 A | 11/1993 | Van Antwerp et al. |
| 5,267,963 A | 12/1993 | Bachynsky |
| 5,269,799 A | 12/1993 | Daniel |
| 5,271,744 A | 12/1993 | Kramer et al. |
| 5,279,579 A | 1/1994 | D'Amico |
| 5,279,591 A | 1/1994 | Simon |
| 5,282,793 A | 2/1994 | Larson |
| 5,300,030 A | 4/1994 | Crossman et al. |
| 5,312,359 A | 5/1994 | Wallace |
| 5,312,369 A | 5/1994 | Arcusin et al. |
| 5,316,246 A | 5/1994 | Scott et al. |
| 5,324,302 A | 6/1994 | Crouse |
| 5,342,319 A | 8/1994 | Watson et al. |
| 5,342,324 A | 8/1994 | Tucker |
| 5,344,007 A | 9/1994 | Nakamura et al. |
| 5,350,392 A | 9/1994 | Purcell et al. |
| 5,354,280 A | 10/1994 | Haber et al. |
| 5,354,337 A | 10/1994 | Hoy |
| 5,366,469 A | 11/1994 | Steg et al. |
| 5,372,592 A | 12/1994 | Gambale |
| 5,372,787 A | 12/1994 | Ritter |
| 5,376,082 A | 12/1994 | Phelps |
| 5,379,895 A | 1/1995 | Foslien |
| 5,384,174 A | 1/1995 | Ward et al. |
| 5,387,197 A | 2/1995 | Smith et al. |
| 5,390,669 A | 2/1995 | Stuart et al. |
| 5,391,151 A | 2/1995 | Wilmot |
| 5,403,288 A | 4/1995 | Stanners |
| 5,405,332 A | 4/1995 | Opalek |
| 5,425,715 A | 6/1995 | Dalling et al. |
| 5,429,607 A | 7/1995 | McPhee |
| 5,429,613 A | 7/1995 | D'Amico |
| 5,439,473 A | 8/1995 | Jorgensen |
| D362,718 S | 9/1995 | Deily et al. |
| 5,449,349 A | 9/1995 | Sallee et al. |
| 5,451,210 A | 9/1995 | Kramer et al. |
| 5,478,316 A | 12/1995 | Bitdinger et al. |
| 5,490,841 A | 2/1996 | Landis |

(56) References Cited

U.S. PATENT DOCUMENTS

| | | |
|---|---|---|
| 5,501,675 A | 3/1996 | Erskine |
| 5,505,709 A | 4/1996 | Funderburk et al. |
| 5,507,730 A | 4/1996 | Haber et al. |
| 5,514,117 A | 5/1996 | Lynn |
| 5,520,654 A | 5/1996 | Wahlberg |
| 5,522,803 A | 6/1996 | Teisson-Simony |
| 5,527,287 A | 6/1996 | Miskinyar et al. |
| 5,533,974 A | 7/1996 | Gaba |
| 5,540,709 A | 7/1996 | Ramel |
| 5,545,143 A | 8/1996 | Fischell |
| 5,545,152 A | 8/1996 | Funderburk et al. |
| 5,549,577 A | 8/1996 | Siegel et al. |
| 5,554,130 A | 9/1996 | McDonald et al. |
| 5,558,650 A | 9/1996 | McPhee |
| 5,562,629 A | 10/1996 | Haughton et al. |
| 5,562,636 A | 10/1996 | Utterberg |
| 5,573,510 A | 11/1996 | Isaacson |
| 5,575,777 A | 11/1996 | Cover et al. |
| 5,584,813 A | 12/1996 | Livingston et al. |
| 5,586,553 A | 12/1996 | Halili |
| 5,591,188 A | 1/1997 | Waisman |
| 5,599,309 A | 2/1997 | Marshall et al. |
| 5,599,315 A | 2/1997 | McPhee |
| 5,599,318 A | 2/1997 | Sweeney et al. |
| 5,628,765 A | 5/1997 | Morita |
| 5,643,214 A | 7/1997 | Marshall |
| 5,643,216 A | 7/1997 | White |
| 5,643,220 A | 7/1997 | Cosme |
| 5,658,256 A | 8/1997 | Shields |
| 5,662,617 A | 9/1997 | Odell et al. |
| 5,665,071 A | 9/1997 | Wyrick |
| 5,665,075 A | 9/1997 | Gyure et al. |
| 5,676,156 A | 10/1997 | Yoon |
| 5,681,323 A | 10/1997 | Arick |
| 5,695,476 A | 12/1997 | Harris |
| 5,697,907 A | 12/1997 | Gaba |
| 5,700,250 A | 12/1997 | Erskine |
| 5,702,371 A | 12/1997 | Bierman |
| 5,704,920 A | 1/1998 | Gyure |
| 5,709,662 A | 1/1998 | Olive et al. |
| 5,714,225 A | 2/1998 | Hansen et al. |
| 5,738,641 A | 4/1998 | Watson et al. |
| 5,741,288 A | 4/1998 | Rife |
| 5,752,923 A | 5/1998 | Terwilliger |
| 5,807,316 A | 9/1998 | Teeple |
| 5,807,348 A | 9/1998 | Zinger et al. |
| 5,810,835 A | 9/1998 | Ryan et al. |
| 5,817,058 A | 10/1998 | Shaw |
| 5,820,598 A | 10/1998 | Gazza et al. |
| 5,827,236 A | 10/1998 | Takahashi |
| 5,833,666 A | 11/1998 | Davis et al. |
| 5,843,001 A | 12/1998 | Goldenberg |
| 5,848,990 A | 12/1998 | Cirelli et al. |
| 5,851,197 A | 12/1998 | Marano et al. |
| 5,858,001 A | 1/1999 | Tsals et al. |
| 5,865,806 A | 2/1999 | Howell |
| 5,899,886 A | 5/1999 | Cosme |
| 5,911,705 A | 6/1999 | Howell |
| 5,913,846 A | 6/1999 | Szabo |
| 5,916,199 A | 6/1999 | Miles |
| 5,919,167 A | 7/1999 | Mulhauser et al. |
| 5,919,170 A | 7/1999 | Woessner |
| 5,925,032 A | 7/1999 | Clements |
| 5,935,109 A | 8/1999 | Donnan |
| 5,947,931 A | 9/1999 | Bierman |
| 5,947,935 A | 9/1999 | Rinehart et al. |
| 5,951,523 A | 9/1999 | Osterlind et al. |
| 5,954,643 A | 9/1999 | VanAntwerp et al. |
| 5,957,892 A | 9/1999 | Thorne |
| 5,957,897 A | 9/1999 | Jeffrey |
| 5,968,011 A | 10/1999 | Larsen et al. |
| 5,971,966 A | 10/1999 | Lav |
| 5,975,120 A | 11/1999 | Novosel |
| 5,980,488 A | 11/1999 | Thorne |
| 5,980,506 A | 11/1999 | Mathiasen |
| 5,984,224 A | 11/1999 | Yang |
| 5,984,897 A | 11/1999 | Peterson et al. |
| D417,733 S | 12/1999 | Howell et al. |
| 6,017,328 A | 1/2000 | Fischell et al. |
| 6,017,598 A | 1/2000 | Kreischer et al. |
| D421,119 S | 2/2000 | Musgrave et al. |
| 6,024,727 A | 2/2000 | Thorne et al. |
| 6,039,629 A | 3/2000 | Mitchell |
| 6,042,570 A | 3/2000 | Bell et al. |
| 6,045,533 A | 4/2000 | Kriesel et al. |
| 6,045,534 A | 4/2000 | Jacobsen et al. |
| 6,050,976 A | 4/2000 | Thorne et al. |
| 6,053,893 A | 4/2000 | Bucher |
| 6,053,930 A | 4/2000 | Ruppert |
| 6,056,718 A | 5/2000 | Funderburk et al. |
| 6,056,726 A | 5/2000 | Isaacson |
| 6,074,369 A | 6/2000 | Sage et al. |
| 6,074,371 A | 6/2000 | Fischell |
| 6,077,244 A | 6/2000 | Botich et al. |
| 6,079,432 A | 6/2000 | Paradis |
| 6,086,008 A | 7/2000 | Gray et al. |
| 6,086,575 A | 7/2000 | Mejslov |
| 6,090,068 A | 7/2000 | Chanut |
| 6,093,172 A | 7/2000 | Funderburk et al. |
| 6,093,179 A | 7/2000 | O'Hara et al. |
| 6,099,503 A | 8/2000 | Stardella |
| 6,105,218 A | 8/2000 | Reekie |
| 6,106,498 A | 8/2000 | Friedli et al. |
| 6,120,482 A | 9/2000 | Szabo |
| 6,123,690 A | 9/2000 | Mejslov |
| 6,132,755 A | 10/2000 | Eicher et al. |
| 6,139,534 A | 10/2000 | Niedospial, Jr. |
| 6,159,181 A | 12/2000 | Crossman et al. |
| 6,183,464 B1 | 2/2001 | Sharp et al. |
| 6,191,338 B1 | 2/2001 | Haller |
| 6,193,694 B1 | 2/2001 | Bell et al. |
| 6,210,420 B1 | 4/2001 | Mauze et al. |
| 6,219,574 B1 | 4/2001 | Cormier et al. |
| 6,221,058 B1 | 4/2001 | Kao et al. |
| 6,248,093 B1 | 6/2001 | Moberg |
| 6,293,925 B1 | 9/2001 | Safabash et al. |
| 6,302,866 B1 | 10/2001 | Marggi |
| 6,319,232 B1 | 11/2001 | Kashmer |
| 6,322,535 B1 | 11/2001 | Hitchins et al. |
| 6,322,808 B1 | 11/2001 | Trautman et al. |
| 6,334,856 B1 | 1/2002 | Allen et al. |
| 6,355,021 B1 | 3/2002 | Nielsen et al. |
| 6,364,113 B1 | 4/2002 | Faasse et al. |
| 6,378,218 B2 | 4/2002 | Sigwart et al. |
| 6,379,335 B1 | 4/2002 | Rigon et al. |
| 6,387,076 B1 | 5/2002 | Van Lunduyt |
| 6,387,078 B1 | 5/2002 | Gillespie, III |
| 6,405,876 B1 | 6/2002 | Seshimoto et al. |
| 6,440,096 B1 | 8/2002 | Lastovich et al. |
| 6,447,482 B1 | 9/2002 | Rønborg et al. |
| 6,450,992 B1 | 9/2002 | Cassidy, Jr. |
| 6,485,461 B1 | 11/2002 | Mason et al. |
| 6,488,663 B1 | 12/2002 | Steg |
| 6,503,222 B2 | 1/2003 | Lo |
| 6,517,517 B1 | 2/2003 | Farrugia et al. |
| 6,520,938 B1 | 2/2003 | Funderburk et al. |
| D472,316 S | 3/2003 | Douglas et al. |
| D472,630 S | 4/2003 | Douglas et al. |
| 6,572,586 B1 | 6/2003 | Wojcik |
| 6,579,267 B2 | 6/2003 | Lynch et al. |
| 6,582,397 B2 | 6/2003 | Alesi et al. |
| 6,595,962 B1 | 7/2003 | Perthu |
| 6,607,509 B2 | 8/2003 | Bobroff et al. |
| 6,607,511 B2 | 8/2003 | Halseth et al. |
| 6,613,064 B2 | 9/2003 | Rutynowski et al. |
| 6,620,133 B1 | 9/2003 | Steck |
| 6,620,136 B1 | 9/2003 | Pressly, Sr. et al. |
| 6,620,140 B1 | 9/2003 | Metzger |
| 6,629,949 B1 | 10/2003 | Douglas |
| 6,645,181 B1 | 11/2003 | Lavi et al. |
| 6,645,182 B1 | 11/2003 | Szabo |
| 6,659,982 B2 | 12/2003 | Douglas et al. |
| 6,685,674 B2 | 2/2004 | Douglas et al. |
| 6,699,218 B2 | 3/2004 | Flaherty et al. |

(56) References Cited

U.S. PATENT DOCUMENTS

| | | | |
|---|---|---|---|
| 6,702,779 B2 * | 3/2004 | Connelly et al. | ............ 604/93.01 |
| 6,726,649 B2 | 4/2004 | Swenson et al. | |
| 6,736,797 B1 | 5/2004 | Larsen et al. | |
| 6,743,203 B1 | 6/2004 | Pickhard | |
| 6,749,587 B2 * | 6/2004 | Flaherty | ........................ 604/151 |
| 6,749,589 B1 | 6/2004 | Douglas et al. | |
| 6,755,805 B1 | 6/2004 | Reid | |
| 6,776,775 B1 | 8/2004 | Mohammad | |
| 6,790,199 B1 | 9/2004 | Gianakos | |
| 6,805,686 B1 | 10/2004 | Fathallah et al. | |
| 6,808,506 B2 | 10/2004 | Lastovich et al. | |
| 6,811,545 B2 | 11/2004 | Vaillancourt | |
| 6,814,720 B2 | 11/2004 | Olsen et al. | |
| 6,824,530 B2 | 11/2004 | Wagner et al. | |
| 6,824,531 B1 | 11/2004 | Zecha, Jr. et al. | |
| 6,830,562 B2 | 12/2004 | Mogensen et al. | |
| 6,837,877 B2 | 1/2005 | Zurcher | |
| 6,837,878 B2 | 1/2005 | Smutney et al. | |
| 6,840,922 B2 | 1/2005 | Nielsen et al. | |
| 6,880,701 B2 | 4/2005 | Bergeron et al. | |
| 6,923,791 B2 | 8/2005 | Douglas | |
| 6,926,694 B2 | 8/2005 | Marano-Ford et al. | |
| 6,939,324 B2 | 9/2005 | Gonnelli et al. | |
| 6,939,331 B2 | 9/2005 | Ohshima | |
| 6,949,084 B2 | 9/2005 | Marggi et al. | |
| 6,959,812 B2 | 11/2005 | Reif et al. | |
| 6,960,193 B2 | 11/2005 | Rosenberg | |
| 6,979,316 B1 | 12/2005 | Rubin et al. | |
| 6,991,619 B2 | 1/2006 | Marano-Ford et al. | |
| 6,991,620 B2 | 1/2006 | Marano-Ford et al. | |
| 6,994,213 B2 | 2/2006 | Giard et al. | |
| 6,997,907 B2 | 2/2006 | Safabash et al. | |
| 7,014,625 B2 | 3/2006 | Bengtsson | |
| 7,018,344 B2 | 3/2006 | Bressler et al. | |
| 7,022,108 B2 | 4/2006 | Marano-Ford et al. | |
| 7,047,070 B2 | 5/2006 | Wilkenson et al. | |
| 7,052,483 B2 | 5/2006 | Wojcik | |
| 7,055,713 B2 | 6/2006 | Rea et al. | |
| 7,056,302 B2 | 6/2006 | Douglas | |
| 7,070,580 B2 | 7/2006 | Nielsen | |
| 7,074,208 B2 | 7/2006 | Pajunk et al. | |
| D526,409 S | 8/2006 | Nielsen et al. | |
| 7,083,592 B2 | 8/2006 | Lastovich et al. | |
| 7,083,597 B2 | 8/2006 | Lynch et al. | |
| 7,097,631 B2 | 8/2006 | Trautman et al. | |
| 7,109,878 B2 | 9/2006 | Mann et al. | |
| 7,115,108 B2 | 10/2006 | Wilkenson et al. | |
| 7,115,112 B2 | 10/2006 | Mogensen et al. | |
| 7,141,023 B2 | 11/2006 | Diermann et al. | |
| 7,147,623 B2 | 12/2006 | Mathiasen | |
| 7,186,236 B2 | 3/2007 | Gibson et al. | |
| 7,211,068 B2 | 5/2007 | Douglas | |
| 7,214,207 B2 | 5/2007 | Lynch et al. | |
| 7,214,215 B2 | 5/2007 | Heinzerling et al. | |
| 7,250,037 B2 | 7/2007 | Shermer et al. | |
| 7,258,680 B2 | 8/2007 | Mogensen et al. | |
| D554,253 S | 10/2007 | Kornerup | |
| 7,303,543 B1 | 12/2007 | Maule et al. | |
| 7,309,326 B2 | 12/2007 | Fangrow, Jr. | |
| 7,322,473 B2 | 1/2008 | Fux | |
| 7,407,491 B2 | 8/2008 | Fangrow, Jr. | |
| 7,407,493 B2 | 8/2008 | Cane' | |
| 7,431,876 B2 | 10/2008 | Mejlhede et al. | |
| 7,441,655 B1 | 10/2008 | Hoftman | |
| 7,569,262 B2 | 8/2009 | Szabo et al. | |
| 7,648,494 B2 | 1/2010 | Kornerup et al. | |
| 7,766,867 B2 | 8/2010 | Lynch et al. | |
| 7,846,132 B2 | 12/2010 | Gravesen et al. | |
| 7,850,652 B2 | 12/2010 | Liniger et al. | |
| 8,012,126 B2 | 9/2011 | Tipsmark et al. | |
| 8,087,333 B2 | 1/2012 | Oishi | |
| 8,123,724 B2 | 2/2012 | Gillespie, III | |
| 8,303,549 B2 | 11/2012 | Mejlhede et al. | |
| 2001/0004970 A1 | 6/2001 | Hollister et al. | |
| 2001/0016714 A1 | 8/2001 | Bell et al. | |
| 2001/0021827 A1 | 9/2001 | Ferguson et al. | |
| 2001/0039387 A1 | 11/2001 | Rutynowski et al. | |
| 2001/0039401 A1 | 11/2001 | Ferguson et al. | |
| 2001/0041875 A1 | 11/2001 | Higuchi et al. | |
| 2001/0049496 A1 | 12/2001 | Kirchhofer | |
| 2001/0053889 A1 | 12/2001 | Marggi | |
| 2001/0056284 A1 | 12/2001 | Purcell et al. | |
| 2002/0022798 A1 | 2/2002 | Connelly | |
| 2002/0022855 A1 | 2/2002 | Bobroff et al. | |
| 2002/0026152 A1 | 2/2002 | Bierman | |
| 2002/0055711 A1 | 5/2002 | Lavi et al. | |
| 2002/0068904 A1 | 6/2002 | Pluth et al. | |
| 2002/0072720 A1 | 6/2002 | Hague et al. | |
| 2002/0074345 A1 | 6/2002 | Scheider et al. | |
| 2002/0077599 A1 | 6/2002 | Wojcik | |
| 2002/0082543 A1 | 6/2002 | Park et al. | |
| 2002/0107489 A1 | 8/2002 | Lee | |
| 2002/0111581 A1 | 8/2002 | Sasso | |
| 2002/0156424 A1 | 10/2002 | Suzuki et al. | |
| 2002/0156427 A1 | 10/2002 | Suzuki et al. | |
| 2002/0161322 A1 | 10/2002 | Utterberg et al. | |
| 2002/0161332 A1 | 10/2002 | Ramey | |
| 2002/0161386 A1 | 10/2002 | Halseth et al. | |
| 2002/0165493 A1 | 11/2002 | Bierman | |
| 2002/0169419 A1 | 11/2002 | Steg | |
| 2002/0173748 A1 | 11/2002 | McConnell et al. | |
| 2002/0173769 A1 | 11/2002 | Gray et al. | |
| 2002/0183688 A1 | 12/2002 | Lastovich et al. | |
| 2002/0189688 A1 | 12/2002 | Roorda | |
| 2002/0193737 A1 | 12/2002 | Popovsky | |
| 2002/0193744 A1 | 12/2002 | Alesi et al. | |
| 2003/0014018 A1 | 1/2003 | Giambattista et al. | |
| 2003/0060781 A1 | 3/2003 | Mogensen et al. | |
| 2003/0069548 A1 | 4/2003 | Connelly et al. | |
| 2003/0088238 A1 * | 5/2003 | Poulsen et al. | ............. 604/890.1 |
| 2003/0105430 A1 | 6/2003 | Lavi et al. | |
| 2003/0109829 A1 | 6/2003 | Mogensen et al. | |
| 2003/0125669 A1 | 7/2003 | Safabash et al. | |
| 2003/0125678 A1 | 7/2003 | Swenson et al. | |
| 2003/0130619 A1 | 7/2003 | Safabash et al. | |
| 2003/0139704 A1 | 7/2003 | Lin | |
| 2003/0158520 A1 | 8/2003 | Safabash et al. | |
| 2003/0176843 A1 | 9/2003 | Wilkinson | |
| 2003/0176852 A1 | 9/2003 | Lynch et al. | |
| 2003/0181863 A1 | 9/2003 | Davis et al. | |
| 2003/0181868 A1 | 9/2003 | Swenson | |
| 2003/0181873 A1 | 9/2003 | Swenson | |
| 2003/0181874 A1 | 9/2003 | Bressler et al. | |
| 2003/0187394 A1 | 10/2003 | Wilkinson et al. | |
| 2003/0187395 A1 | 10/2003 | Gabel | |
| 2003/0199823 A1 | 10/2003 | Bobroff et al. | |
| 2003/0216686 A1 | 11/2003 | Lynch et al. | |
| 2003/0220610 A1 | 11/2003 | Lastovich et al. | |
| 2003/0225373 A1 | 12/2003 | Bobroff et al. | |
| 2003/0225374 A1 | 12/2003 | Mathiasen | |
| 2003/0229308 A1 | 12/2003 | Tsals et al. | |
| 2003/0229316 A1 | 12/2003 | Hwang et al. | |
| 2004/0002682 A1 | 1/2004 | Kovelman et al. | |
| 2004/0006316 A1 | 1/2004 | Patton | |
| 2004/0044306 A1 | 3/2004 | Lynch et al. | |
| 2004/0049159 A1 | 3/2004 | Barrus et al. | |
| 2004/0059316 A1 | 3/2004 | Smedegaard | |
| 2004/0068231 A1 | 4/2004 | Blondeau | |
| 2004/0069044 A1 | 4/2004 | Lavi et al. | |
| 2004/0087913 A1 | 5/2004 | Rogers et al. | |
| 2004/0092865 A1 | 5/2004 | Flaherty et al. | |
| 2004/0092875 A1 | 5/2004 | Kochamba | |
| 2004/0111068 A1 | 6/2004 | Swenson | |
| 2004/0112781 A1 | 6/2004 | Hofverberg et al. | |
| 2004/0116865 A1 | 6/2004 | Bengtsson | |
| 2004/0133164 A1 | 7/2004 | Funderburk et al. | |
| 2004/0138612 A1 | 7/2004 | Shermer et al. | |
| 2004/0138620 A1 | 7/2004 | Douglas et al. | |
| 2004/0143216 A1 | 7/2004 | Douglas et al. | |
| 2004/0143218 A1 | 7/2004 | Das | |
| 2004/0158202 A1 | 8/2004 | Jensen | |
| 2004/0158207 A1 | 8/2004 | Hunn et al. | |
| 2004/0162518 A1 | 8/2004 | Connelly et al. | |
| 2004/0162521 A1 | 8/2004 | Bengtsson | |

(56) References Cited

U.S. PATENT DOCUMENTS

| | | |
|---|---|---|
| 2004/0171989 A1 | 9/2004 | Horner et al. |
| 2004/0178098 A1 | 9/2004 | Swenson et al. |
| 2004/0186446 A1 | 9/2004 | Ohshima |
| 2004/0193143 A1 | 9/2004 | Sauer |
| 2004/0199123 A1 | 10/2004 | Nielsen |
| 2004/0204673 A1 | 10/2004 | Flaherty et al. |
| 2004/0204687 A1 | 10/2004 | Mogensen et al. |
| 2004/0204690 A1 | 10/2004 | Yashiro et al. |
| 2004/0215151 A1 | 10/2004 | Marshall et al. |
| 2004/0220528 A1 | 11/2004 | Garcia, Jr. |
| 2004/0236284 A1 | 11/2004 | Hoste et al. |
| 2004/0238392 A1 | 12/2004 | Peterson et al. |
| 2004/0243065 A1 | 12/2004 | McConnell et al. |
| 2004/0254433 A1 | 12/2004 | Bandis et al. |
| 2004/0260235 A1 | 12/2004 | Douglas |
| 2004/0260250 A1 | 12/2004 | Harris et al. |
| 2005/0035014 A1 | 2/2005 | Cane |
| 2005/0038378 A1 | 2/2005 | Lastovich et al. |
| 2005/0043687 A1 | 2/2005 | Mogensen et al. |
| 2005/0049571 A1 | 3/2005 | Lastovich et al. |
| 2005/0065466 A1 | 3/2005 | Vedrine |
| 2005/0065472 A1 | 3/2005 | Cindrich et al. |
| 2005/0075606 A1 | 4/2005 | Botich et al. |
| 2005/0080386 A1 | 4/2005 | Reid |
| 2005/0101910 A1 | 5/2005 | Bowman et al. |
| 2005/0101912 A1 | 5/2005 | Faust et al. |
| 2005/0101932 A1 | 5/2005 | Cote et al. |
| 2005/0101933 A1 | 5/2005 | Marrs et al. |
| 2005/0107743 A1 | 5/2005 | Fangrow, Jr. |
| 2005/0113761 A1 | 5/2005 | Faust et al. |
| 2005/0119611 A1 | 6/2005 | Marano-Ford et al. |
| 2005/0119619 A1 | 6/2005 | Haining |
| 2005/0119637 A1 | 6/2005 | Lundgren et al. |
| 2005/0124936 A1 | 6/2005 | Mogensen et al. |
| 2005/0131347 A1 | 6/2005 | Marano-Ford et al. |
| 2005/0159709 A1 | 7/2005 | Wilkinson |
| 2005/0159714 A1 | 7/2005 | Gibson |
| 2005/0165382 A1 | 7/2005 | Fulford |
| 2005/0192560 A1 | 9/2005 | Walls et al. |
| 2005/0203461 A1 | 9/2005 | Flaherty et al. |
| 2005/0215979 A1 | 9/2005 | Kornerup et al. |
| 2005/0240154 A1 | 10/2005 | Mogensen et al. |
| 2005/0251098 A1 | 11/2005 | Wyss et al. |
| 2005/0256456 A1 | 11/2005 | Marano-Ford et al. |
| 2005/0261629 A1 | 11/2005 | Marano-Ford et al. |
| 2005/0277892 A1 | 12/2005 | Chen |
| 2005/0283114 A1 | 12/2005 | Bresina et al. |
| 2006/0015063 A1 | 1/2006 | Butikofer et al. |
| 2006/0015076 A1 | 1/2006 | Heinzerling et al. |
| 2006/0030815 A1 | 2/2006 | Csincsura et al. |
| 2006/0036214 A1 | 2/2006 | Mogensen et al. |
| 2006/0041224 A1 | 2/2006 | Jensen |
| 2006/0069351 A9 | 3/2006 | Safabash et al. |
| 2006/0069382 A1 | 3/2006 | Pedersen |
| 2006/0069383 A1 | 3/2006 | Bogaerts et al. |
| 2006/0095003 A1 | 5/2006 | Marano-Ford et al. |
| 2006/0095014 A1 | 5/2006 | Ethelfeld |
| 2006/0106346 A1 | 5/2006 | Sullivan et al. |
| 2006/0129123 A1 | 6/2006 | Wojcik |
| 2006/0135908 A1 | 6/2006 | Liniger et al. |
| 2006/0135913 A1 | 6/2006 | Ethelfeld |
| 2006/0142698 A1 | 6/2006 | Ethelfeld |
| 2006/0161108 A1 | 7/2006 | Mogensen et al. |
| 2006/0173410 A1 | 8/2006 | Moberg et al. |
| 2006/0173413 A1 | 8/2006 | Fan |
| 2006/0184104 A1 | 8/2006 | Cheney, II et al. |
| 2006/0184140 A1 | 8/2006 | Okiyama |
| 2006/0200073 A1 | 9/2006 | Radmer et al. |
| 2006/0241551 A1 | 10/2006 | Lynch et al. |
| 2006/0247553 A1 | 11/2006 | Diermann et al. |
| 2006/0247574 A1 | 11/2006 | Maule et al. |
| 2006/0253085 A1 | 11/2006 | Geismar et al. |
| 2006/0253086 A1 | 11/2006 | Moberg et al. |
| 2006/0264835 A1* | 11/2006 | Nielsen et al. ............... 604/174 |
| 2006/0264890 A1 | 11/2006 | Moberg et al. |
| 2007/0005017 A1 | 1/2007 | Alchas et al. |
| 2007/0016129 A1 | 1/2007 | Liniger et al. |
| 2007/0016159 A1 | 1/2007 | Sparholt et al. |
| 2007/0021729 A1 | 1/2007 | Mogensen et al. |
| 2007/0049865 A1 | 3/2007 | Radmer et al. |
| 2007/0049870 A1 | 3/2007 | Gray et al. |
| 2007/0051784 A1 | 3/2007 | Money et al. |
| 2007/0066955 A1 | 3/2007 | Sparholt et al. |
| 2007/0088271 A1 | 4/2007 | Richards et al. |
| 2007/0093754 A1 | 4/2007 | Mogensen |
| 2007/0104596 A1 | 5/2007 | Preuthun et al. |
| 2007/0112301 A1 | 5/2007 | Preuthun et al. |
| 2007/0112303 A1 | 5/2007 | Liniger |
| 2007/0129688 A1 | 6/2007 | Scheider et al. |
| 2007/0173767 A1 | 7/2007 | Lynch et al. |
| 2007/0179444 A1 | 8/2007 | Causey et al. |
| 2007/0185441 A1 | 8/2007 | Fangrow, Jr. |
| 2007/0191772 A1 | 8/2007 | Wojcik |
| 2007/0191773 A1 | 8/2007 | Wojcik |
| 2007/0203454 A1 | 8/2007 | Shermer et al. |
| 2007/0213673 A1 | 9/2007 | Douglas |
| 2007/0244448 A1 | 10/2007 | Lastovich et al. |
| 2007/0299409 A1 | 12/2007 | Whitbourne et al. |
| 2008/0269687 A1 | 10/2008 | Chong |
| 2008/0312601 A1 | 12/2008 | Cane' |
| 2009/0062767 A1 | 3/2009 | Van Antwerp et al. |
| 2009/0326456 A1 | 12/2009 | Cross et al. |
| 2010/0004597 A1 | 1/2010 | Gyrn et al. |
| 2010/0137829 A1 | 6/2010 | Nielsen et al. |
| 2010/0228226 A1 | 9/2010 | Nielsen |
| 2010/0262078 A1 | 10/2010 | Blomquist |

FOREIGN PATENT DOCUMENTS

| | | |
|---|---|---|
| DE | 299 05 072 U1 | 9/1999 |
| DE | 101 17 285 A1 | 11/2002 |
| DE | 203 20 207 U1 | 11/2004 |
| EP | 0117632 B1 | 9/1984 |
| EP | 0239244 B1 | 2/1987 |
| EP | 0272530 A2 | 6/1988 |
| EP | 0451040 A1 | 10/1991 |
| EP | 0544837 B1 | 6/1993 |
| EP | 0615768 A2 | 9/1994 |
| EP | 0651662 B1 | 5/1995 |
| EP | 0652027 A1 | 5/1995 |
| EP | 0657184 A1 | 6/1995 |
| EP | 0688232 A1 | 12/1995 |
| EP | 0714631 B1 | 6/1996 |
| EP | 0744183 A2 | 11/1996 |
| EP | 0747006 A1 | 12/1996 |
| EP | 0799626 A1 | 10/1997 |
| EP | 0 937 475 A2 | 8/1999 |
| EP | 0956879 A1 | 11/1999 |
| EP | 1086718 A1 | 3/2001 |
| EP | 1125593 A1 | 8/2001 |
| EP | 0775501 B1 | 6/2002 |
| EP | 1329233 A1 | 7/2003 |
| EP | 1350537 A1 | 10/2003 |
| EP | 1360970 A1 | 11/2003 |
| EP | 1380315 A1 | 1/2004 |
| EP | 1407747 A1 | 4/2004 |
| EP | 1407793 A1 | 4/2004 |
| EP | 1421968 A2 | 5/2004 |
| EP | 1177802 B1 | 9/2004 |
| EP | 1475113 A1 | 11/2004 |
| EP | 1 495 775 A1 | 1/2005 |
| EP | 1502613 A1 | 2/2005 |
| EP | 1525873 A1 | 4/2005 |
| EP | 1 527 792 A1 | 5/2005 |
| EP | 1527792 A1 | 5/2005 |
| EP | 1559442 A2 | 8/2005 |
| EP | 1616594 A1 | 1/2006 |
| EP | 1704889 A1 | 9/2006 |
| EP | 1719537 A2 | 11/2006 |
| EP | 1762259 A1 | 3/2007 |
| EP | 1764125 A1 | 3/2007 |
| EP | 1776980 A1 | 4/2007 |
| EP | 1970091 A1 | 9/2008 |
| EP | 2272559 A1 | 1/2011 |

(56) References Cited

FOREIGN PATENT DOCUMENTS

| | | |
|---|---|---|
| FR | 2725902 A1 | 10/1994 |
| GB | 906574 | 9/1962 |
| GB | 2 088 215 A | 6/1982 |
| GB | 2 230 702 A | 10/1990 |
| GB | 2 423 267 A | 8/2006 |
| GB | 2 450 872 A | 7/2007 |
| JP | 10179734 A | 8/1991 |
| JP | 7051251 A | 11/1995 |
| JP | 8187286 A | 7/1996 |
| JP | 03-191965 A | 7/1998 |
| JP | 2002-028246 A | 1/2002 |
| RU | 2 238 111 C2 | 12/2003 |
| SU | 933 100 | 6/1982 |
| WO | WO 81/01795 A1 | 7/1981 |
| WO | WO 82/03558 A1 | 10/1982 |
| WO | WO 92/04062 A1 | 3/1992 |
| WO | WO 93/05840 A2 | 4/1993 |
| WO | WO 93/11709 A1 | 6/1993 |
| WO | WO 94/20160 A1 | 9/1994 |
| WO | WO 95/19194 A1 | 7/1995 |
| WO | WO 96/32981 A1 | 7/1996 |
| WO | WO 96/20021 A1 | 10/1996 |
| WO | WO 98/26835 A1 | 6/1998 |
| WO | WO 98/33549 A1 | 8/1998 |
| WO | WO 98/58693 A1 | 12/1998 |
| WO | WO 99/07435 A1 | 2/1999 |
| WO | WO99/22789 A1 | 5/1999 |
| WO | WO 99/33504 A1 | 7/1999 |
| WO | WO 00/02614 A1 | 1/2000 |
| WO | WO 00/03757 A1 | 1/2000 |
| WO | WO 00/44324 A1 | 8/2000 |
| WO | WO 01/12746 A1 | 2/2001 |
| WO | WO 01/30419 A2 | 5/2001 |
| WO | WO 01/68180 A1 | 9/2001 |
| WO | WO 01/72353 A2 | 10/2001 |
| WO | WO 01/76684 A1 | 10/2001 |
| WO | WO 01/93926 A2 | 12/2001 |
| WO | WO 02/02165 A2 | 1/2002 |
| WO | WO 02/07804 A1 | 1/2002 |
| WO | WO 02/40083 A2 | 5/2002 |
| WO | WO 02/40083 A2 | 5/2002 |
| WO | WO 02/053220 A2 | 7/2002 |
| WO | WO 02/081012 A2 | 10/2002 |
| WO | WO 02/081013 A2 | 10/2002 |
| WO | WO 02/083206 A2 | 10/2002 |
| WO | WO 02/094352 A2 | 11/2002 |
| WO | WO 02/100457 A2 | 12/2002 |
| WO | WO 02/102442 A1 | 12/2002 |
| WO | WO 02/068014 A3 | 1/2003 |
| WO | WO 03/015860 A1 | 2/2003 |
| WO | WO 03/026728 A1 | 4/2003 |
| WO | WO 03/068305 A1 | 8/2003 |
| WO | WO 03/075980 A2 | 9/2003 |
| WO | WO 03/095003 A1 | 11/2003 |
| WO | WO 2004/012796 A1 | 2/2004 |
| WO | WO 2004/026375 A1 | 4/2004 |
| WO | WO 2004/029457 A1 | 4/2004 |
| WO | WO 2004/030726 A1 | 4/2004 |
| WO | WO 2004/037325 A1 | 5/2004 |
| WO | WO 2004/054644 A1 | 7/2004 |
| WO | WO 2004/056412 A2 | 7/2004 |
| WO | WO 2004/064593 A2 | 8/2004 |
| WO | WO 2004/071308 A1 | 8/2004 |
| WO | WO 2004/087240 A1 | 10/2004 |
| WO | WO 2004/098683 A1 | 11/2004 |
| WO | WO 2004/101016 A1 | 11/2004 |
| WO | WO 2004/101071 A2 | 11/2004 |
| WO | WO 2004/110527 A1 | 12/2004 |
| WO | WO 2005/002649 A1 | 1/2005 |
| WO | WO 2005/004973 A1 | 1/2005 |
| WO | WO 2005/018703 A2 | 3/2005 |
| WO | WO 2005/037184 A2 | 4/2005 |
| WO | WO 2005/037350 A2 | 4/2005 |
| WO | WO 2005/039673 A2 | 5/2005 |
| WO | WO 2005/046780 A1 | 5/2005 |
| WO | WO 2005/065748 A1 | 7/2005 |
| WO | WO 2005/068006 A1 | 7/2005 |
| WO | WO 2005/072795 A2 | 8/2005 |
| WO | WO 2005/092410 A1 | 10/2005 |
| WO | WO 2005/094920 A1 | 10/2005 |
| WO | WO 2005/118055 A1 | 12/2005 |
| WO | WO 2006/003130 A1 | 1/2006 |
| WO | WO 2006/015507 A2 | 2/2006 |
| WO | WO 2006/015600 A2 | 2/2006 |
| WO | WO 2006/024650 A2 | 3/2006 |
| WO | WO 2006/032689 A1 | 3/2006 |
| WO | WO 2006/032692 A1 | 3/2006 |
| WO | WO 2006/061027 A2 | 6/2006 |
| WO | WO 2006/061354 A1 | 6/2006 |
| WO | WO 2006/062680 A1 | 6/2006 |
| WO | WO 2006/062912 A1 | 6/2006 |
| WO | WO 2006/075016 A1 | 7/2006 |
| WO | WO 2006/077262 A1 | 7/2006 |
| WO | WO 2006/077263 A1 | 7/2006 |
| WO | WO 2006/089958 A1 | 8/2006 |
| WO | WO 2006/097111 A2 | 9/2006 |
| WO | WO 2006/108775 A2 | 10/2006 |
| WO | WO 2006/120253 A2 | 11/2006 |
| WO | WO 2006/121921 A2 | 11/2006 |
| WO | WO 2006/122048 A1 | 11/2006 |
| WO | WO 2007/000162 A2 | 1/2007 |
| WO | WO 2007/002523 A2 | 1/2007 |
| WO | WO 2007/020090 A1 | 2/2007 |
| WO | WO 2007/065944 A1 | 6/2007 |
| WO | WO 2007/071255 A1 | 6/2007 |
| WO | WO 2007/071258 A1 | 6/2007 |
| WO | WO 2007/093051 A1 | 8/2007 |
| WO | WO 2007/093182 A2 | 8/2007 |
| WO | WO 2007/122207 A1 | 11/2007 |
| WO | WO 2007/140631 A1 | 12/2007 |
| WO | WO 2007/140783 A2 | 12/2007 |
| WO | WO 2007/140785 A1 | 12/2007 |
| WO | WO 2007/141210 A1 | 12/2007 |
| WO | WO 2008/014791 A1 | 2/2008 |
| WO | WO 2008/014792 A1 | 2/2008 |
| WO | WO 2008/048631 A1 | 4/2008 |
| WO | WO 2008/052545 A1 | 5/2008 |
| WO | WO 2008/065646 A1 | 6/2008 |
| WO | WO 2008/092782 A1 | 8/2008 |
| WO | WO 2008/092958 A1 | 8/2008 |
| WO | WO 2008/092959 A1 | 8/2008 |
| WO | WO 2008/135098 A1 | 11/2008 |
| WO | WO 2008/148714 A1 | 12/2008 |
| WO | WO 2008/155145 A1 | 12/2008 |
| WO | WO 2008/155377 A1 | 12/2008 |
| WO | WO 2009/004026 A1 | 1/2009 |
| WO | WO 2009/007287 A1 | 1/2009 |
| WO | WO 2009/010396 A1 | 1/2009 |
| WO | WO 2009/010399 A1 | 1/2009 |
| WO | WO 2009/016635 A2 | 2/2009 |
| WO | WO 2009/098291 A1 | 8/2009 |
| WO | WO 2009/098306 A1 | 8/2009 |
| WO | WO 2009/101130 A1 | 8/2009 |
| WO | WO 2009/101145 A1 | 8/2009 |
| WO | WO 2009/103759 A1 | 8/2009 |
| WO | WO 2009/106517 A1 | 9/2009 |
| WO | WO 2009/144272 A1 | 12/2009 |
| WO | WO 2010/003885 A1 | 1/2010 |
| WO | WO 2010/003886 A1 | 1/2010 |
| WO | WO 2010/030602 A1 | 3/2010 |
| WO | WO 2010/034830 A1 | 4/2010 |
| WO | WO 2010/072664 A1 | 7/2010 |
| WO | WO 2010/112521 A1 | 10/2010 |
| WO | WO 2011/012465 A1 | 2/2011 |
| WO | WO 2011/015659 A1 | 2/2011 |
| WO | WO 2011/121023 A1 | 10/2011 |

OTHER PUBLICATIONS

International-Type Search Report for Danish Application No. DK 2006/00103 completed Sep. 20, 2006.
International Search Report for International Application No. PCT/DK2006/000737 completed Feb. 14, 2007.

* cited by examiner

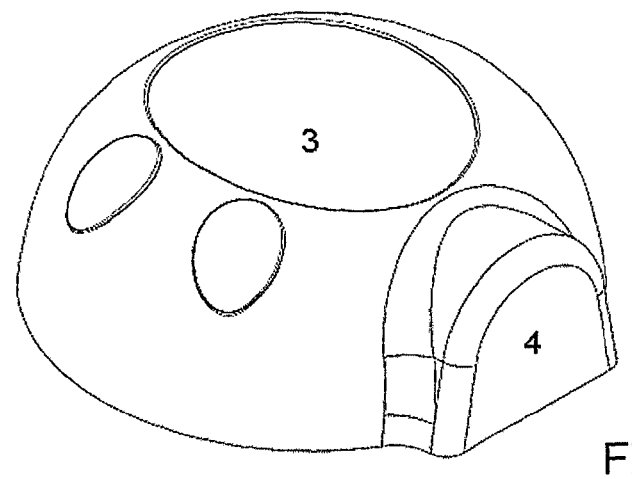
Fig. 20
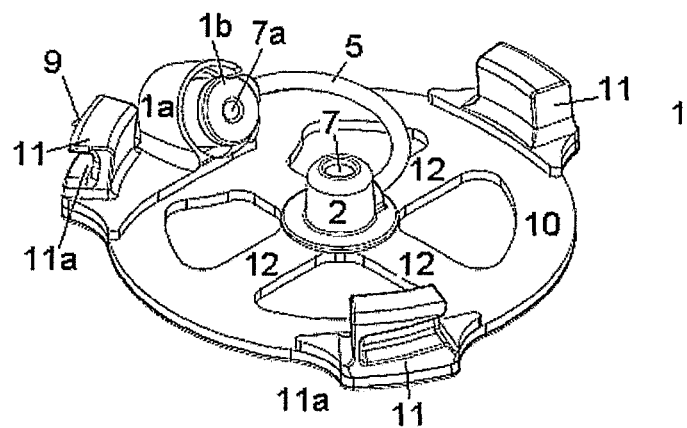
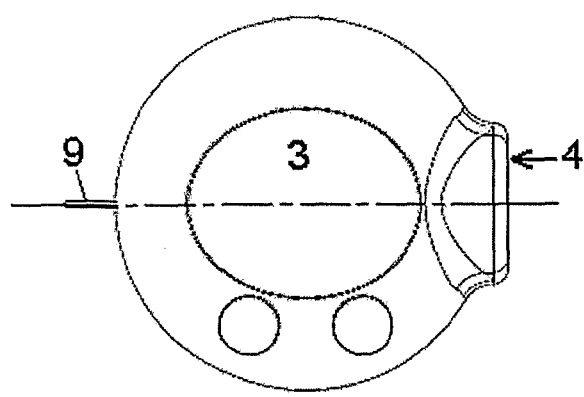
Fig. 21
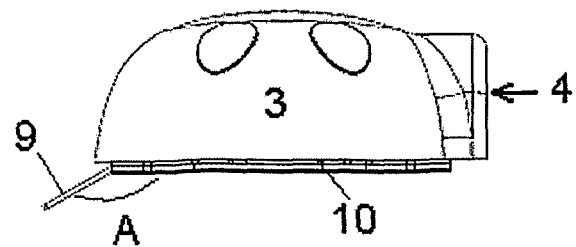

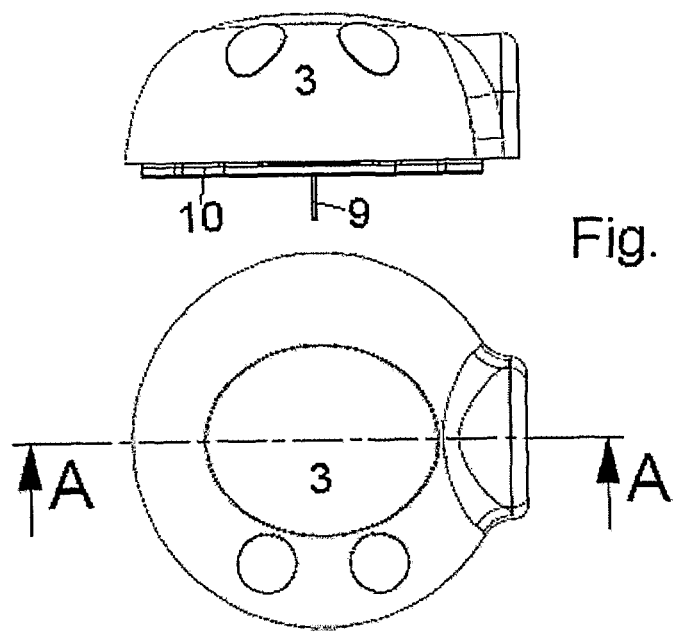
Fig. 27
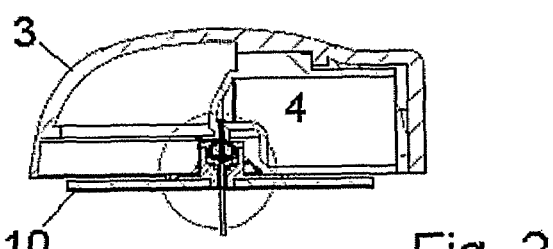
Fig. 28
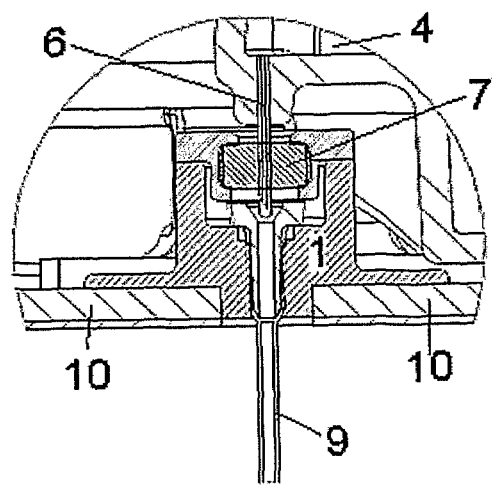

DEVICE FOR ADMINISTRATION

This application claims the benefit under 35 U.S.C. §371 of International Application No. PCT/DK2006/000737, filed Dec. 22, 2006, which claims the benefit of U.S. Provisional Application Ser. No. 60/753,684, filed Dec. 23, 2005, Danish Patent Application No. PA 2006 00103, filed Jan. 24, 2006, and U.S. Provisional Application Ser. No. 60/762,231, filed Jan. 25, 2006 and 60/816,767, filed Jun. 27, 2006. These references are incorporated herein in their entirety.

THE TECHNICAL FIELD

The invention relates to a device for an intermittent or continuous administration of a therapeutical substance, such as insulin, comprising an injection part and a fluid delivery part. The fluid delivery part normally comprises a reservoir, transferal means e.g. in form of a pump and a house, and the injection part normally comprises a base plate, a cannula part comprising a cannula extending past the proximal side of the base plate and means for fixation of the base plate to the skin of the user.

PRIOR ART

Both EP-A1-1.527.792 and EP-A1-1.495.775 describe a medical device comprising a transdermal access unit and a reservoir. The transdermal access unit comprises transdermal access means for transporting a fluid through a skin portion of a subject, and a mounting surface adapted for application to the skin of the subject. The reservoir unit comprises a reservoir adapted to contain a fluid drug and an outlet allowing the transdermal access means to be arranged in fluid communication with an interior of the reservoir. Also the device comprise means for expelling e.g. a pump which means during use expels a fluid drug out of the reservoir and through the skin of the subject via the transdermal access means. The transdermal access unit and the reservoir unit further comprise releasable mating coupling means allowing the reservoir unit to be secured to the transdermal access unit during use. The object of the invention is to provide a skin mountable drug delivery device or system which allows such a device or system to be used in a convenient and cost-effective manner.

According to this document the insertion needle (113, 212 or 412) of the described embodiments is pivotably arranged inside the needle housing and can be moved between an extended and an extracted position. When the injection needle is inserted it penetrates a membrane in order to penetrate the skin of the subject. After the needle has been inserted there is no flexible effect in the system.

US 2004/0204673 A1 describes a lightweight and low cost fluid delivery device capable of adjustable and programmable fluid delivering; the device includes a housing that surrounds a reservoir chamber. A dispenser is in fluid communication with the reservoir chamber for dispensing the fluid from the reservoir in finite amounts. The dispenser is controlled by an electronic microcontroller of the fluid delivery device. The fluid delivery device further includes a communication element that receives information from a remote control device not mechanically attached to the fluid delivery device of the present invention. Also included is an exit port assembly in fluid communication with the dispenser from which the liquid medication exits the fluid delivery device and enters the body of a mammalian patient transcutaneously.

The housings 702, 802 can each be made from flexible material, or can be provided with flexible hinged sections that allow the fluid delivery device 10 to flex during patient movement to prevent detachment and aid in patient comfort but there are no directions as to how such a hinged section should be constructed.

THE INVENTION

The object of the invention is to provide a device for delivering fluid including a pump, a reservoir and an injection part which device assures less discomfort to the wearer during use. The devices according to the present invention are constructed with means to reduce the transferal of actions from the relatively heavy delivering part to the injection part when the delivering part is affected by touches or movements.

According to claim 1 the invention comprises a device for delivering fluid comprising an injection part and a fluid delivery part where the fluid delivery part comprises a reservoir, transferal means e.g. in form of a pump and a house, and the injection part comprises a base plate, a cannula part comprising a body providing a through-going opening leading liquid to a cannula which cannula extends past the proximal side of the base plate and means for fixation of the base plate to the skin of the user wherein a flexible part is arranged in an area between the subcutaneously positioned section of the cannula and the fluid delivery part.

That a part is flexible means that it is resilient, able to be deformed without breaking, non-rigid, it is not purely a rigid material moving from one position to another, it has a certain degree of elasticity such that when one end of the flexible part is subjected to external influencing factors e.g. pushing and pulling effects these external effects are not transferred directly to the cannula when the cannula is inserted but the effects are at least partly absorbed. The flexibility need not be a result of the material characteristic but can be a result of the physical structure of the material e.g. the material is corrugated or the like. As the delivery part is susceptible for external influencing factors such as pulling and pushing effects when the user is moving around, it is desirable that these effects are not transferred to the cannula which is positioned through the user's skin. The flexible part will at least partly absorb these effects and assure that the cannula is not influenced i.e. pulled out or moved around thereby causing discomfort or pain for the user.

According to one embodiment the flexible part is integrated in the base plate according to this embodiment the base plate can be constructed either partially or completely by a flexible material.

According to a second embodiment the flexible part is integrated in the body of the cannula part providing a through-going opening leading liquid to a cannula according to this embodiment the body of the cannula part can be constructed either partially or completely by a flexible material.

According to a third embodiment the flexible part is integrated in the fluid delivery part.

According to a fourth embodiment the flexible part is a separate unit placed between the fluid delivery part and the injection part. According to this embodiment the separate unit can be constructed either partially or completely by a flexible material.

That the cannula part and/or a base plate and/or a separate unit is/are constructed partially by a flexible material can mean that a fraction of the full area of the part/plate/unit is e.g. made by a different material or made with a structure such as holes, which structure increases the elasticity of the material in one or more dimensions. If the part/plate/unit is constructed completely by a flexible material the choice of material together with the dimensions of the material e.g. the thickness of the part/plate/unit and/or the form of the periphery will define the flexibility.

A suitable flexible material for each of the mentioned units would be an elastomer.

When the flexible part is a separate unit it forms an interface between the injection part and the delivery part thereby providing a flexible transition which provides absorption of the transferable effects originating from the weight and volume of the fluid delivery device.

According to one embodiment the fluid delivery part and the injection part can be separated and rejoined.

According to one embodiment the base plate is provided with fastening means for connecting and disconnecting of the delivery device extending from the distal side of the base plate.

According to one embodiment the house of the fluid delivery part also provides a house for the injection part.

When the house is provided by the fluid delivery part it is possible for the user to visually check the complete fluid path as the house of the fluid delivery part can provide a fully removable protective cover. Also it is possible to create the flexible base part without a house or protective cover which could make the base part less flexible.

According to one embodiment the flexible part is constructed of an area with reduced material dimensions. "Reduced material dimensions" could be both reduction of thickness i.e. "height" of the material and reduction of transverse section i.e. "width" of the material.

According to a second embodiment the flexible part is constructed of an area made by a softer and more flexible/elastic material.

According to a third embodiment the flexible part is constructed of an area made of a material which by its form has an ability for extension and compression such as a material being pleated or folded or corrugated.

According to one embodiment the cannula and the delivery part are not interconnected by non-flexible areas.

According to one embodiment a fluid tight connection leading fluid from the reservoir to the cannula is formed when the delivery part and the injection part are joined together.

According to one embodiment the access of micro organisms to the reservoir of the fluid delivery part during periods when the fluid delivery part and the injection part are separated is prevented as the opening to the reservoir is blocked when the two parts are separated.

According to one embodiment the reservoir has two positions, a first position and a second position, in the first position the outlet from the reservoir is blocked with a first barrier which is not permeable for microorganisms and the inlet of the through-going opening in the cannula part is blocked with a second barrier which is not permeable for microorganisms, in the second position an open fluid connection is formed between the reservoir and the through-going opening in the cannula part by passing the first and the second barrier. According to this embodiment one or both of the barriers comprise a material which can be penetrated by a needle-like object where the opening close on retraction of the needle-like object. The needle-like object can be blunt or sharp-pointed. One or both of the barriers can comprise a hard surface which is moved forming an opening in the area positioned between the outlet of the outlet pipe and the inlet of the through-going fluid path.

According to one embodiment the means for fixation of the base plate to the skin of the user comprises a mounting pad adhered to the proximal side of the base plate and/or to the proximal side of the cannula part.

According to one embodiment the base plate has the form of a lattice with a peripheral coherent part and one or more bars interconnecting the peripheral part. The base plate can have a round or oval peripheral part and the bars have one end attached to the peripheral area and a second end attached to a central area. The base plate can have three or more bars.

According to one embodiment the base plate is not provided with a cannula holding part before use e.g. the base plate is provided with an opening through which a cannula holding part can be inserted.

According to one embodiment the cannula at one end is provided with a body which body comprises solid walls and a protective seal protecting the fluid entrance to the cannula.

According to one embodiment injection part comprising the base plate is provided with a first part of a cannula part acting as positioning controller for a second part which second part comprises a cannula and is to be inserted with an injection needle.

The cannula can be inserted with an inserter device provided with means corresponding to the surface of the base plate, and when said means of the inserter device are combined with the corresponding surface of the base plate, the inserter device is positioned in such way that the cannula, e.g. a cannula including a body, is inserted predictably and correct in relation to the base part. E.g. a first part of the cannula part is provided with means for locking a second part in a desired position.

According to one embodiment the base plate is unreleasably connected to a mounting pad.

A "reservoir" is the part of a device where the liquid is held, the liquid being any kind of medication which has to be delivered to the patient in a certain amount at certain time intervals. The "delivery part" is the part of the device which holds a liquid storage and assures transport of the liquids to the injection part by pumping and e.g. controlling the amount of added liquid. The "injection part" defines a kind of port which is fastened to the users skin and provided with means e.g. a cannula for transferring the liquid to the user and the injection part do not comprise any heavy or voluminous parts. The injection part can comprise two or more separable parts, where one or more parts are unreleasably connected to the base part and one or more parts can be fastened to the base part before or after fastening of the base part to the skin of the patient.

When the flexible areas are placed between the relatively heavy delivery device and the injection device, the transferal of actions from the delivery device to the injection device is prevented or at least significantly reduced, and the injection site of the subcutaneously placed cannula will be protected from the main part of any interaction resulting from pushing or touching the delivery part. Often the delivery part is separated physically from the injection part by a relatively long tube which prevents the transferal of actions but when the delivery part is positioned together with the injection device, the user will feel less discomfort when wearing a device according to the invention.

By using a connector it is possible to avoid the direct contact between the delivery part and the injection part and at the same time fasten both parts as one unit to the skin of the patient.

The cannula can protrude from the proximal side of the body of the injection part or from the side of the body. If the cannula protrudes from the side of the body as it does in the embodiments shown in FIG. 4 and FIG. 7, the cannula will normally be bending and it would be preferred to use a cannula which is at least partly formed of a soft and flexible material. If the cannula protrudes from the proximal side of the body as shown in FIG. 12, the cannula can be made of a hard material such as metal or it can be made of a soft and flexible material.

According to the invention the connector needle can be one end of a single needle which at the other end functions as the cannula. When the connector needle and the cannula is formed as one needle, the needle is normally made of metal or hard polymer but it can also be made of e.g. a polymer which is hardened in the connector end and unhardened and soft in the cannula end. Also the single needle can be composed of two different materials, a hard material for the connector end and a relatively soft material for the cannula end. Also the connector needle and the cannula can be separated into at least two needles. The injector part can then be provided with a commonly known soft cannula which cannula can be inserted by the help of an insertion needle attached to a separate inserter, and the connector needle can be made of a hard material and fastened to either the injector part or the delivery part.

The flexible areas are constructed of an area with reduced material dimensions, e.g. openings or cuts can be provided in a material or the thickness of a material can be reduced, or of an area made by a softer and more flexible material or it is constructed of an area made of a material which by its form or structure has ability for extension and compression such as a material being pleated or folded.

Access of micro organisms to the reservoir during a non-connected state, i.e. when the reservoir and the injection part are separated, is prevented as the opening to the reservoir is blocked when the two parts separate. When e.g. a connector needle is attached to the delivery device the opening in the septum of the connector will close upon removal of the connector needle.

In another embodiment the reservoir of the delivery part has two positions, a first position and a second position, in the first position the outlet from the reservoir is blocked with a first barrier which is not permeable for micro organisms and the inlet of the through going opening in the injection part is blocked with a second barrier which is not permeable for micro organisms, in the second position an open fluid connection is formed between the reservoir and the through going opening in the injection part by passing the first and the second barrier. The word "passing" comprise all possible ways to make a flow pass through or around a barrier, in most of the described embodiments of this invention the barrier is passed by penetrating the barrier with a needle but there is also an example (FIGS. 18A and B) where the barrier is passed by pushing aside a cover thereby creating a flow path.

If the barriers comprise a material which can be penetrated by a needlelike object, where the opening close on retraction of the needle like object, the needlelike object can be either blunt or sharp-pointed meaning that the needlelike object either pushes its way through the barrier or cuts its way through the barrier.

In another embodiment at least one of the barriers comprise a hard surface, i.e. a surface which cannot be penetrated by at least a blunt needle, which is moved forming an opening in the area positioned between the outlet of the outlet pipe and the inlet of the through going fluid path.

The device is often fastened to the patients skin by applying a mounting pad to the proximal side of the base part or to the proximal side of the infusion part, the adhering of the mounting pad to the base part or infusion part can include glue, Velcro, molding etc.

In one embodiment the base part has the form of a lattice with. The peripheral part can either be formed with opening or be formed as a coherent part constituting the circumference of the base part. That the base part has the form of a lattice means that is formed of one or more bars interconnecting with each other and with the peripheral part if present. A base part of this form can easily be provided with a desired flexibility and can take any desired form which might be needed in order to fit the injection part and the delivery part to the mounted device.

In one embodiment the injection part is constructed of at least two separable parts where the first part is unreleasably connected to the base part and the second part comprising the cannula is placed in the first part before or after mounting of the base part on the skin of the patient. The partitioning of the injection part has the advantage that it makes applying of the device much more flexible. The second part can comprise a relatively small body where from a cannula extend from the proximal end and a septum protects the distal end. The second part can e.g. be sold together with a base part already being mounted in an inserter.

If the injection part is constructed of more than one separable part the first part can be provided with means for locking the second part in a desired position. Also the second part can be provided with means for locking the second part to the first part in a desired position or the first and the second part can each be provided with corresponding locking means.

Embodiments of the invention will now be described with reference to the figures in which:

FIG. 20 shows a sixth embodiment having a base part equipped with a central connector and peripheral injection part.

FIG. 21 shows the delivery device and the base part of the sixth embodiment in a joined state from above and from the side.

FIG. 27 shows the delivery device and the base part of the seventh embodiment in a joined state from the side and from above.

FIG. 28 shows a cut through view of the seventh embodiment in the joined state of FIG. 27 and an enlargement of the combined connector/injection part.

Figure 39A:
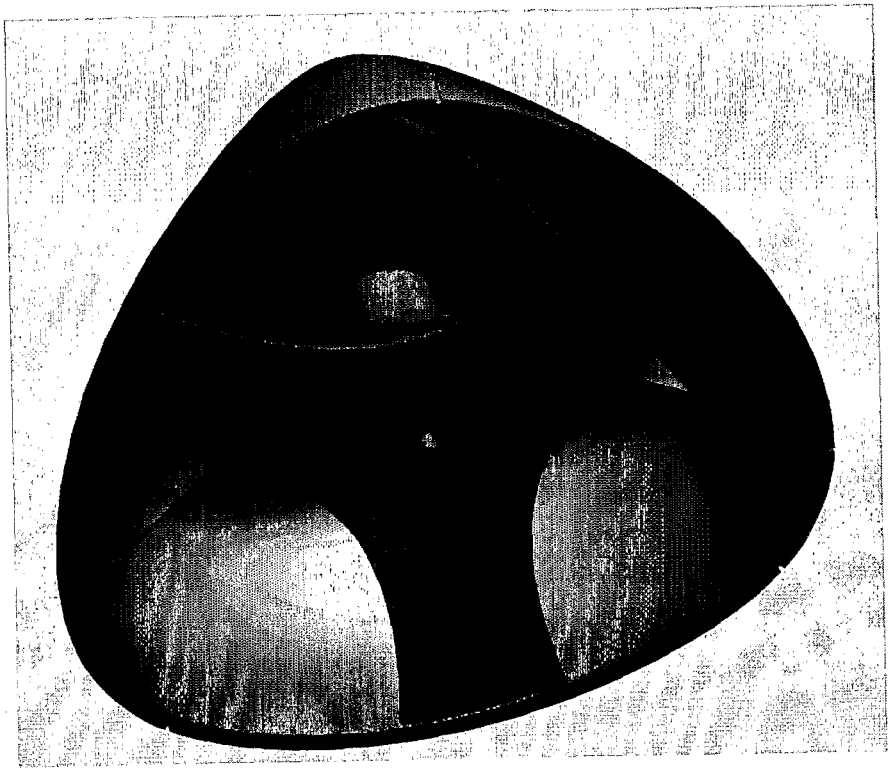
Figure 39B:
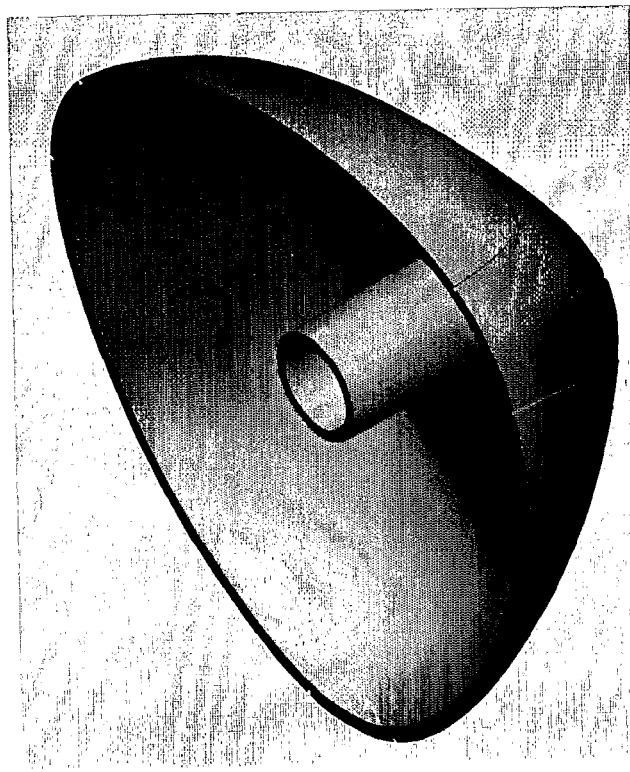

FIGS. 39a and 39b both shows the delivery part of the tenth embodiment seen from below, in FIG. 39 a the injection part without a mounting pad and the delivery part are joined, and in 39b only the delivery part is shown.

Figure 40:
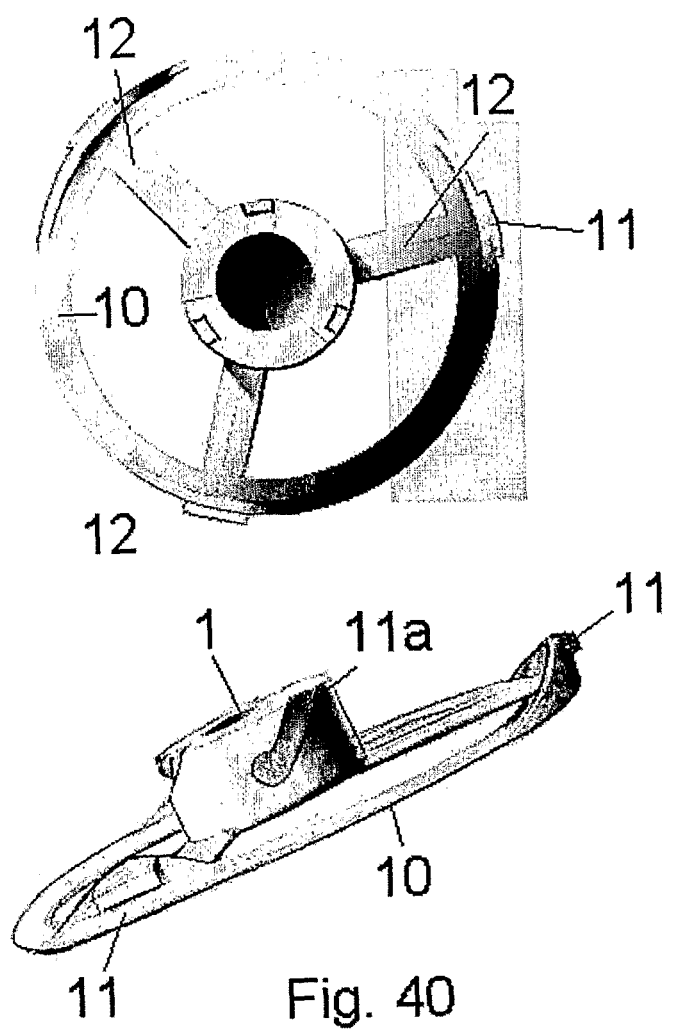

FIG. 40 shows an embodiment of the injection part having the fastening means for the delivery part placed centrally and peripherally.

Figure 41A:
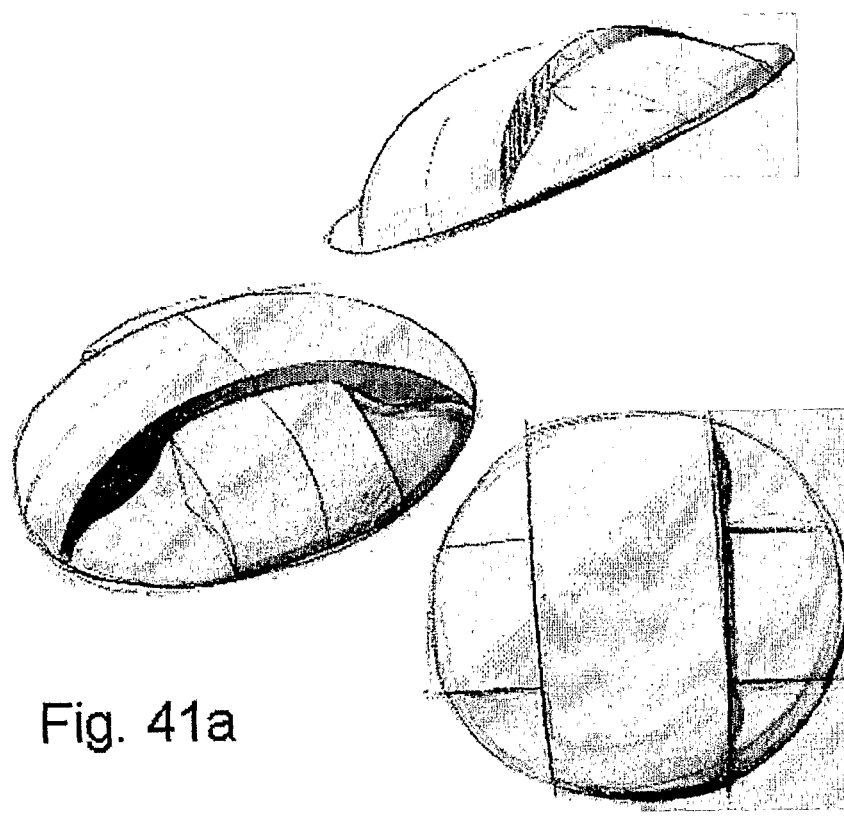
Figure 41B:
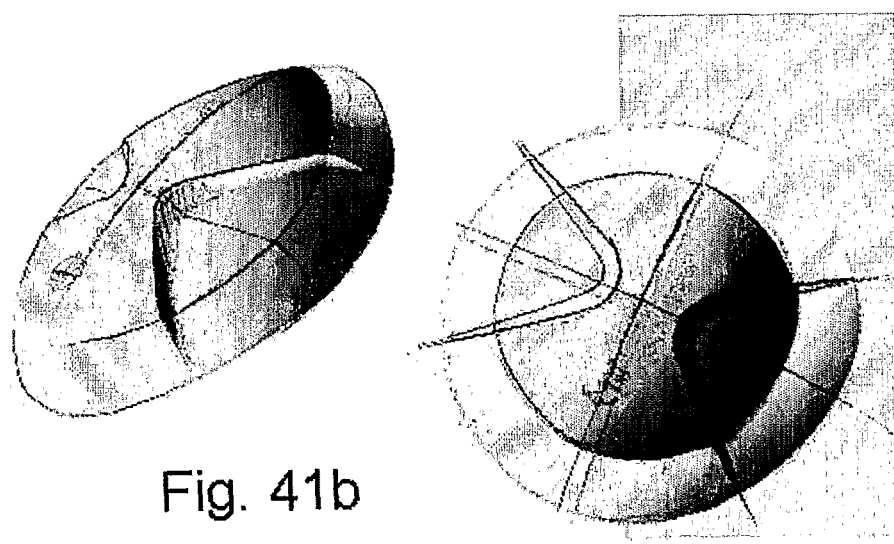

FIG. 41a-b shows different embodiments of the house of the delivery part which also function as house for the injection part.

Figure 1:
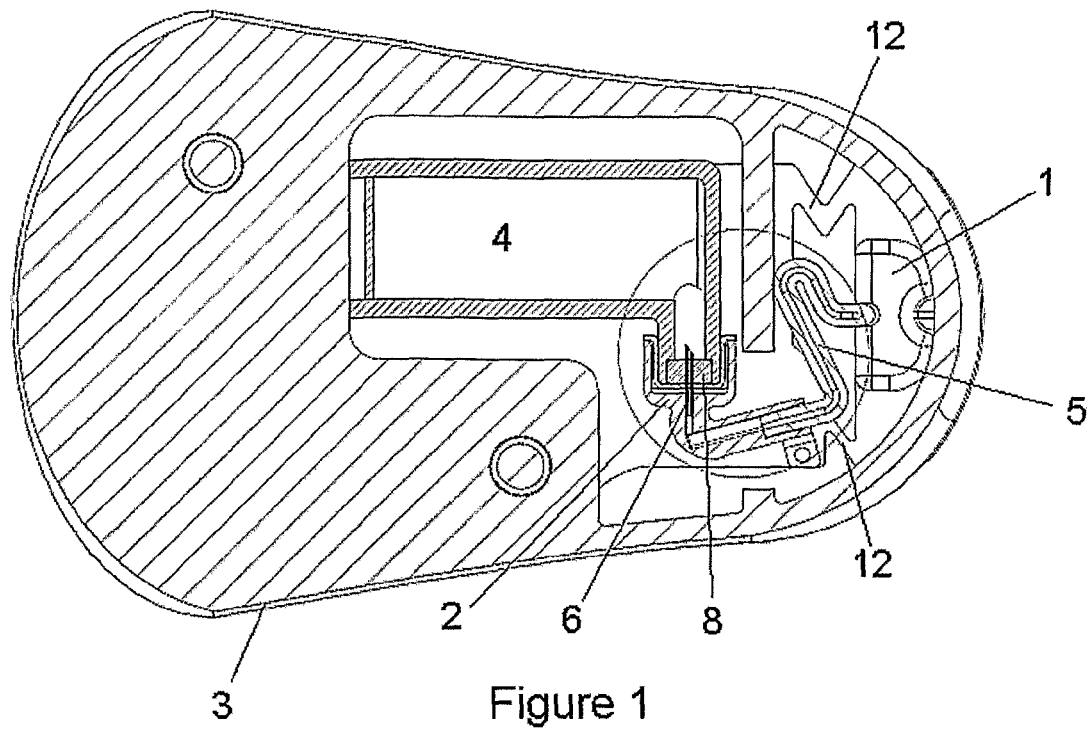
FIG. 1 shows a first embodiment of the invention from above at the B-B line shown in FIG. 3, where the delivery part is placed beside the injection part.
Figure 2:
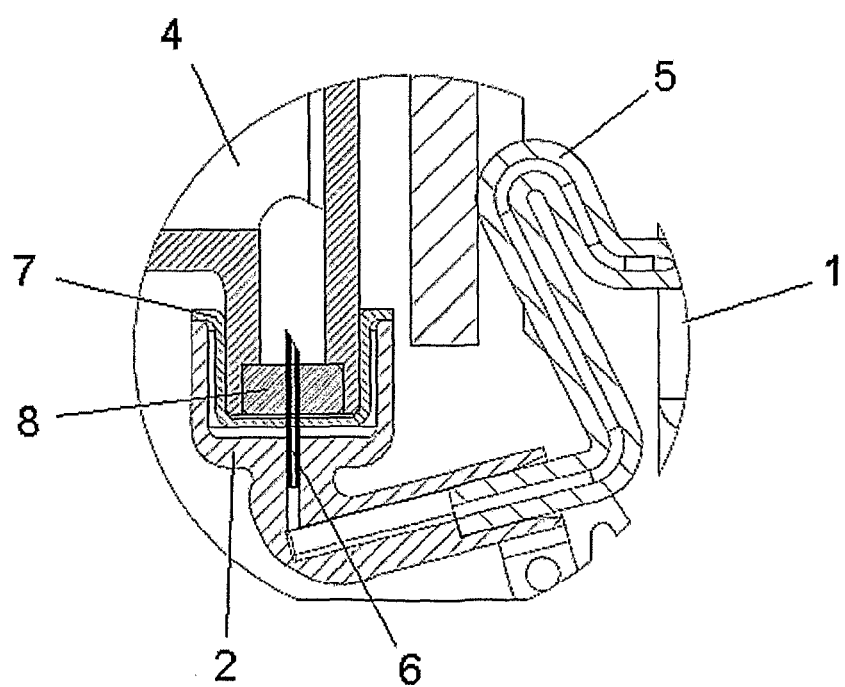
FIG. 2 shows an enlarged part, marked with a circle, of the embodiment in FIG. 1.
Figure 3:
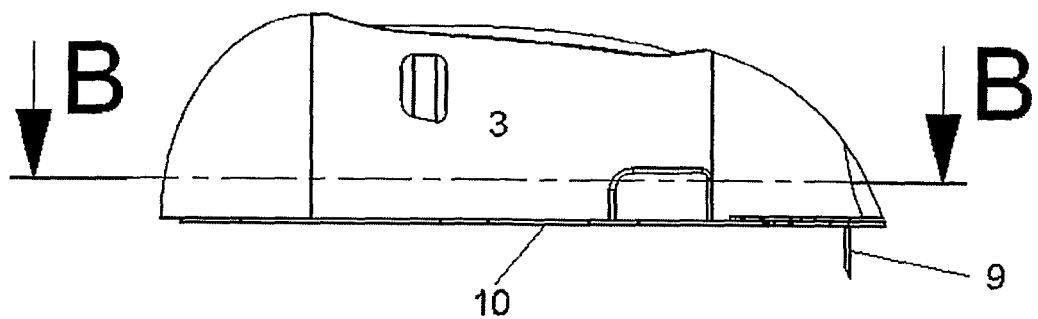
FIG. 3 shows the embodiment of FIG. 1 from the side indicating the line B-B.

FIGS. 1-3 show a first embodiment of a device according to the invention where the delivery part and the injection part are fastened to each other. In FIG. 1 the embodiment is seen from above at the B-B line shown in FIG. 3 and FIG. 2 show a small part of FIG. 1 in enlarge form. The device comprises an injection part which injection part comprises a base plate 10 which is not visible at FIG. 1, a cannula part 1 and a not shown mounting unit, normally a mounting pad. The cannula part 1 comprises a body providing a through-going opening leading liquid to a cannula 9 which after insertion is positioned subcutaneously. The device further comprises a connector 2 and a delivery part provided with a smooth cover 3, the delivery part comprises a not shown pump and a reservoir 4. A flexible tube 5 creates a fluid connection between the injection part and the delivery part and a connector needle 6 which can penetrate both a protective seal 7 covering the entrance of the connector 2 and a septum 8 covering the entrance of the reservoir secures the fluid path way from the delivery part to the injection part. In FIG. 1-3 the device is in a connected state where the injection part and the delivery part are joined together and ready for use.

FIG. 2 shows an enlargement of the connector 2 of FIG. 1. In this embodiment the connector 2 comprises a molded part in a non-flexible material with a through-going opening which in one end is connected to the flexible tube 5 and in the other end is provided with a connector needle 6. In a state where the connector 2 is not connected to the reservoir 4, the connector needle 6 extends into a closed room comprising walls formed respectively of a cylindrical extension of the connector 2 and of the elastic protective seal 7. In the connected state the protective seal 7 is pushed towards the inside wall of the connector 2 surrounding the connector needle 6 and when connecting the connector 2 to the reservoir 4 the connector needle 6 first penetrates the protective seal 7 and then the septum 8 in order to create a passage from the connector 2 to the inside of the reservoir 4. In this embodiment the connector 2 is fastened unreleasably to a base plate 10 which is an integrated part of the injection part.

FIG. 3 shows the embodiment of FIG. 1 from the side as it would look when the device is in use. A base plate 10 is placed along the skin of the patient and fastened to the patient e.g. by an adhesive pad. The cannula 9 protrudes from the proximal side of the base plate 10 below the injection part and the injection part is covered by a house 3 provided by the delivery part 3, 4. The delivery part 3, 4 is fastened to the distal side of the base plate 10 beside the injection part and is also covered by the house 3.

The base plate 10 will normally at the proximal side be fastened to the patient by an adhesive part or layer but any kind of mounting which will make the base plate 10 stick to the patient without allowing the device to move can be used. The adhesive part or layer can be fastened to the base plate 10 by glue, Velcro, molding or the like.

In a preferred embodiment the delivery part is fastened to the distal side of the base plate 10 by one or more magnets which are embedded in the base plate 10. The detachable delivery part has corresponding magnets which keeps the delivery part in position during use. By means of the magnets of the base plate 10 and/or the delivery part 3, 4 it will be possible to detect conditions of the system such as whether the delivery part is secured properly, if the flow through the device is acceptable, how long has the delivery part been fastened to the base plate, size of the volume which has passed the device, etc.

Figure 4:
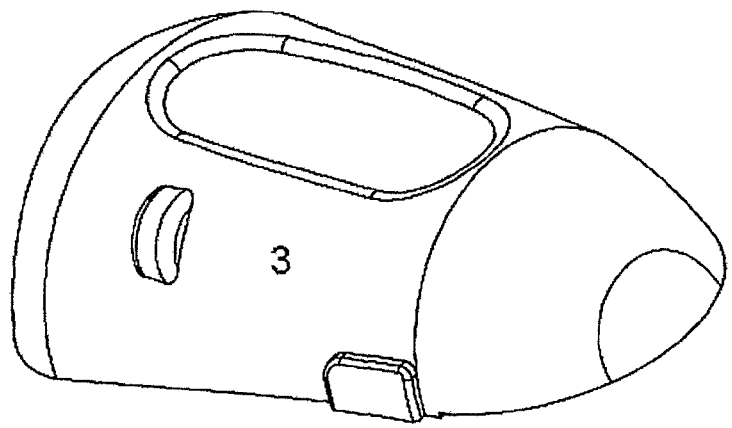
FIG. 4 shows the first embodiment where the delivery part is separated from the injection part.
Figure 4:
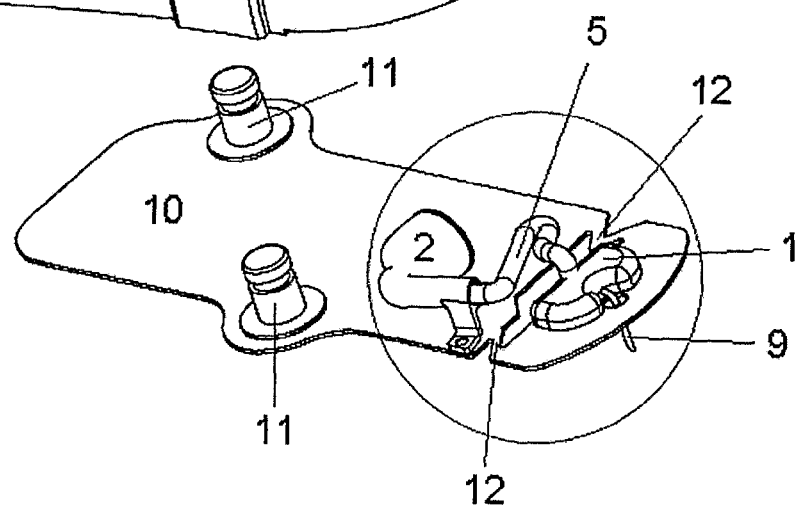

FIG. 4 shows the first embodiment in a separated state where it is possible to see the base plate 10 to which the injection part 1 is fastened, objects 11 for fastening of the delivery part to the base plate 10 and a flexible portion 12 of the base plate 10. In order to fastened the delivery part to the base part 10 the delivery part 3, 4 is pushed down towards the base part 10 from above. The flexible portion 12 is constructed of two thin connections formed as straight lines and made by removing material from the plane of the base part 10. This construction of the base part 10 together with the flexible tube 5 allows the subcutaneously injected cannula 9 to remain in a stationary position although the delivery part which is fastened to the opposite end of the base part 10 is touched or pushed or just moves as a result of the movements of the user.

Figure 5:
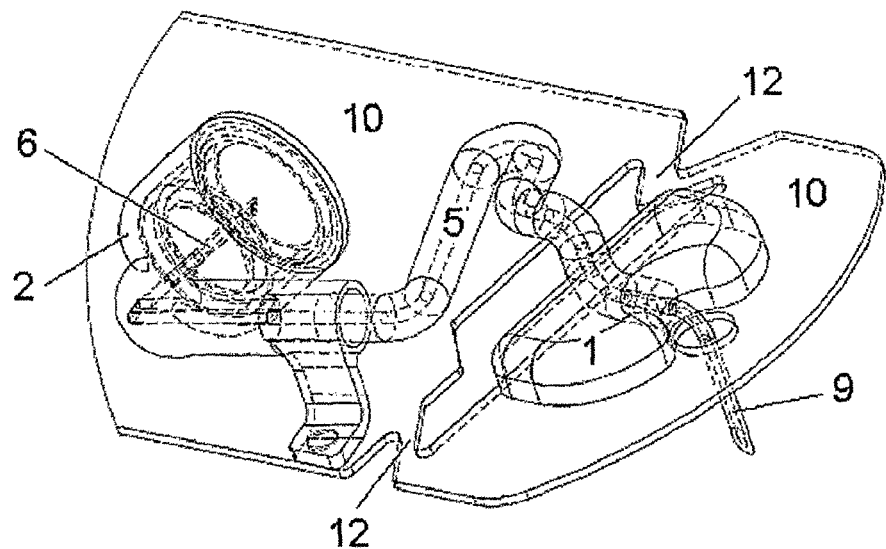
FIG. 5 shows an enlarged part, marked with a circle, of the embodiment in FIG. 4.

FIG. 5 shows an enlargement of a part of the first embodiment of FIG. 4. FIG. 5 shows in greater detail how the cannula 9 is held in position by the body of the cannula part 1; the injection part is via the flexible tube 5 connected to the connector 2. The connector 2, which is fastened to the base part 10 on the same side of the base part 10 as the delivery part, is shown in a transparent form which makes it possible to see the connector needle 6. The connector 2 is preferably made of PP, ABS or similar materials.

In the first embodiment described in FIG. 1-5 one of the flexible areas between the delivery part 3, 4 and the injection part 1 is formed by the flexible tube 5. The flexible tube can be produced as a piece of extruded tube, and can be made of PUR (polyurethane), PP (polypropylene), PE (polyethylene), silicone or any other material which is adequately flexible or can be brought into a flexible form e.g. by providing the tube with folding.

The cannula 9 can together with the rest of the injection part be inserted subcutaneously either by the help of an inserter or manually.

The house 3 of the delivery part 3, 4 is made of a relatively hard material such as PP or ABS (Poly (Acrylo nitrile, Butadiene, Styrene)) which makes it possible for the house to resist impacts of the surroundings.

Figure 6A:
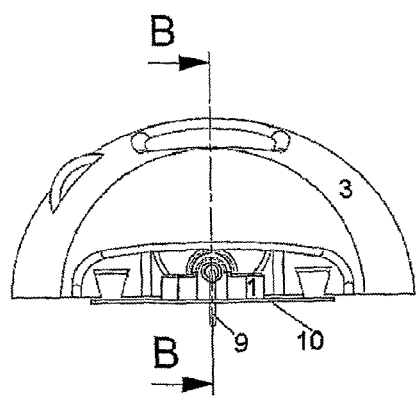
FIG. 6A shows a second embodiment of the invention seen from the side of the injection part.
Figure 6B:
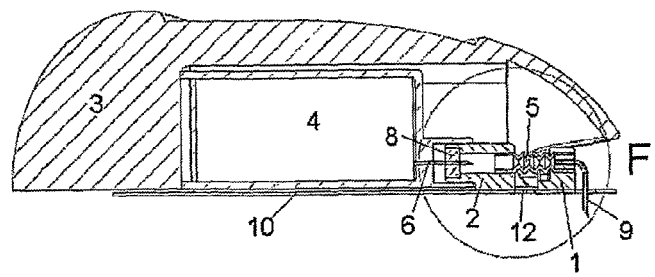
FIG. 6B shows the same embodiment as in FIG. 6A seen from the cut made by the line B-B.
Figure 7:
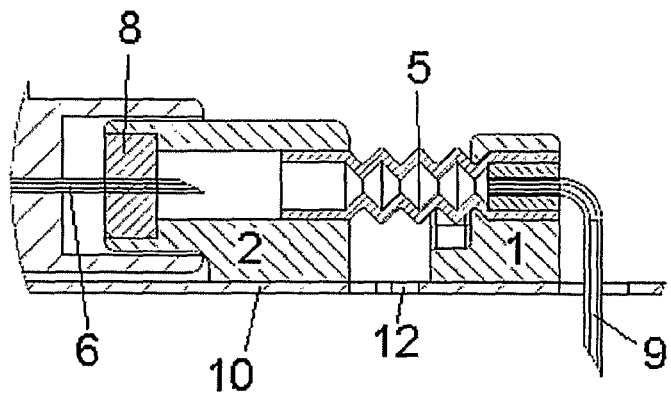
FIG. 7 shows an enlarged part, marked with a circle, of the embodiment in FIG. 6B.

FIG. 6A shows a second embodiment of the device for delivering fluid according to the invention seen from the side facing the injection part. FIG. 6B shows the same embodiment seen from a cut through the device at the line B-B. FIG. 7 shows an enlargement of the section of the embodiment connecting the injection part to the delivery part 3, 4 through the connector 2. In FIGS. 6A, 6B and 7 the delivery part and the injection part are both connected to the base part 10 which is the state of the device when in use.

In the second embodiment the injection part 1 is connected to the delivery part 3, 4 by a flexible tube 5 which in this embodiment is formed as a bellows and preferably is made of silicone, PUR, PP/PE or the like. The flexible portions 12 of the base part 10 is formed as relatively thin V-shaped connections made by removing material from the plane of the base part 10. This embodiment is provided with sliding rails 11 acting as objects for fastening of the delivery part 3, 4 to the base part 10. In this embodiment the connector needle 6 is fastened to the delivery part 3, 4. The connector needle 6 penetrates a septum 7 when the delivery part is joined to the connector 2 and thereby creates a flow path from the reservoir 4 to the cannula 9.

Figures 8A, 8B:
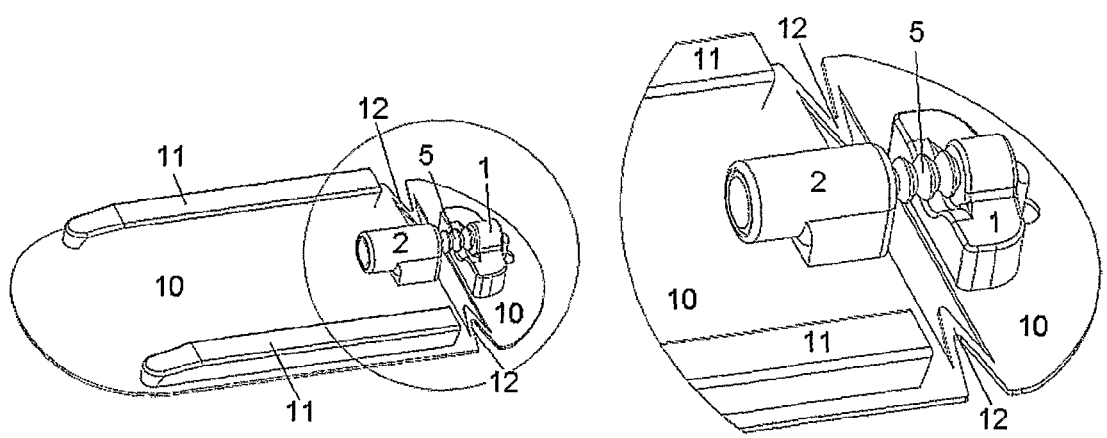
FIG. 8A shows the injection part and the base part of the second embodiment separated from the delivery part.
FIG. 8B shows an enlarged part, marked with a circle, of the embodiment in FIG. 8A.

FIGS. 8A and 8B shows the embodiment in a state where the delivery part 3, 4 is separated from the base part 10 which makes it possible to see the two sliding rails 11.

In FIG. 8B is shown an enlargement of the connector 2 of FIG. 8A. In this embodiment the connector 2 comprises a molded part in a non-flexible material with a through-going opening which in one end is connected to the flexible tube 5 and in the other end is provided with a septum 7. The flexibility of the flexible tube 5 can be obtained be using a soft and flexible material but in this embodiment the flexibility of the tube 5 is obtained by constructing the flexible tube 5 of a stable—that is a rather rigid—and corrugated material. The reservoir 4 is provided with a connector needle 6 and a cylindrical extension which extension protects the connector needle 6 and can be provided with a protective seal (not shown in FIG. 8B). In a state where the connector 2 is not connected to the reservoir 4, the connector needle 6 extends into a closed room comprising walls formed by the cylindrical extension of the reservoir 4 and possibly of a not shown elastic protective seal. In the connected state the protective seal if present is pushed towards the inside wall of the reservoir 4 surrounding the connector needle 6 and when connecting the connector 2 to the reservoir 4 the connector needle 6 first penetrates the protective seal and then the septum 7 in order to create a passage from the reservoir 4 to the inside of the connector 2. In this embodiment the connector 2 is fastened unreleasably to the base plate 10 which is an integrated part of the delivery part 3, 4.

Figure 9:
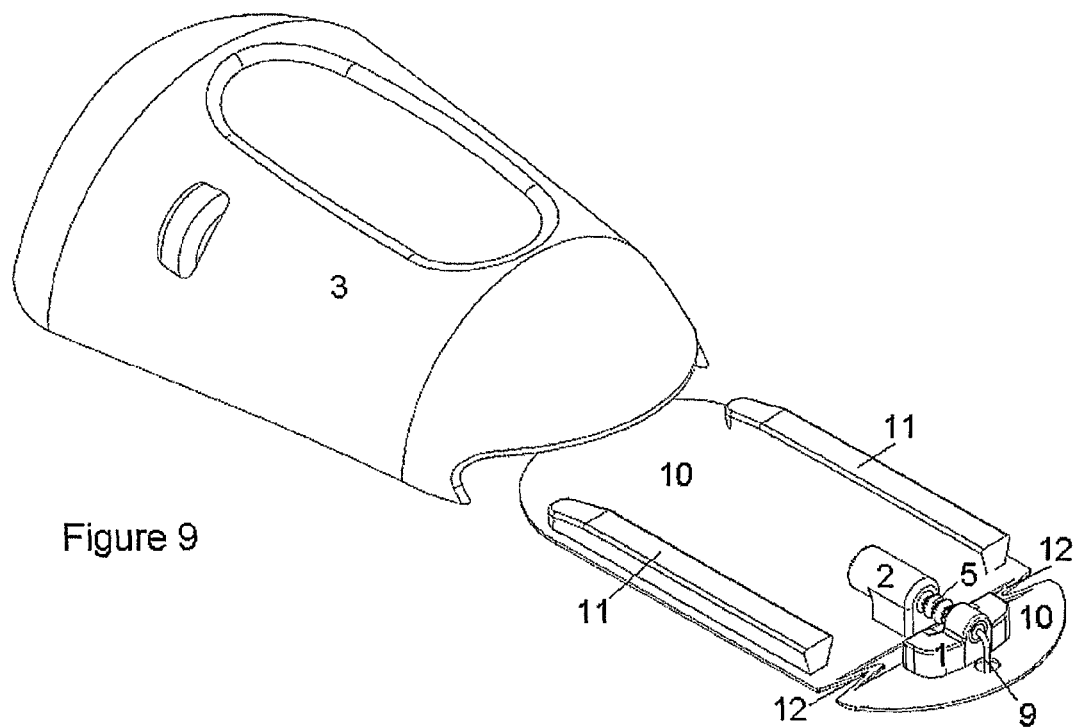
FIG. 9 shows both the delivery part and the injection part of the second embodiment.
Figure 10A:
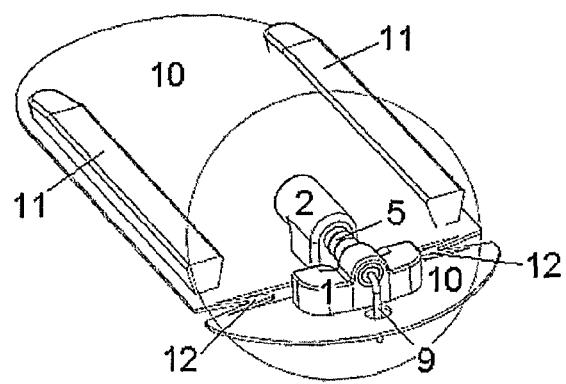
FIG. 10A shows the same embodiment as FIG. 8A from a different angle.
Figure 10B:
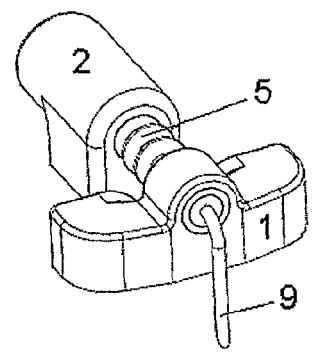
FIG. 10B shows an enlarged part, marked with a circle, of the embodiment in FIG. 10A.

FIGS. 9, 10A and 10B also show the device according to the second embodiment of the invention. FIG. 9 shows the delivery part 3, the base part 1 and the injection part and how they are positioned relatively to each other just before they are being joined and an arrow indicates the direction of movement when the delivery device 3, 4 is fastened to the objects 11 of the base part 10 in order to form a connection to the injection part 1. FIG. 10A shows the same embodiment as FIG. 8A from a different angle and FIG. 10B shows an enlargement of the connector 2, marked with a circle, of the embodiment in FIG. 10A. In this embodiment the cannula 9 protrudes laterally from the injector device and has been inserted perpendicularly to the users' skin. If the cannula 9 is made of a soft and flexible material it is necessary to use an insertion needle to penetrate the skin of the user. This can be done manually by providing the device with an insertion needle protruding through the proximal opening of the cannula 9. The sharp insertion needle exits from the proximal end of the cannula 9 and it is either entering the distal end of the cannula, e.g. through a septum covering the distal opening of the cannula 9, or it is entering the cannula through the side. In case the insertion needle enters the cannula 9 through the side it is necessary to provide the entering position with some kind of a closure in order to prevent micro organisms to enter the device when the insertion needle is removed after insertion. This embodiment of the device can be inserted with an inserter e.g. the inserter known from PCT application no. DK2005/050010 filed on Dec. 9, 2005. If the cannula was protruding from the proximal side of the injection part it could e.g. have been inserted with the inserter known from PCT application DK02/00640 filed on Sep. 27, 2002.

Figure 11:
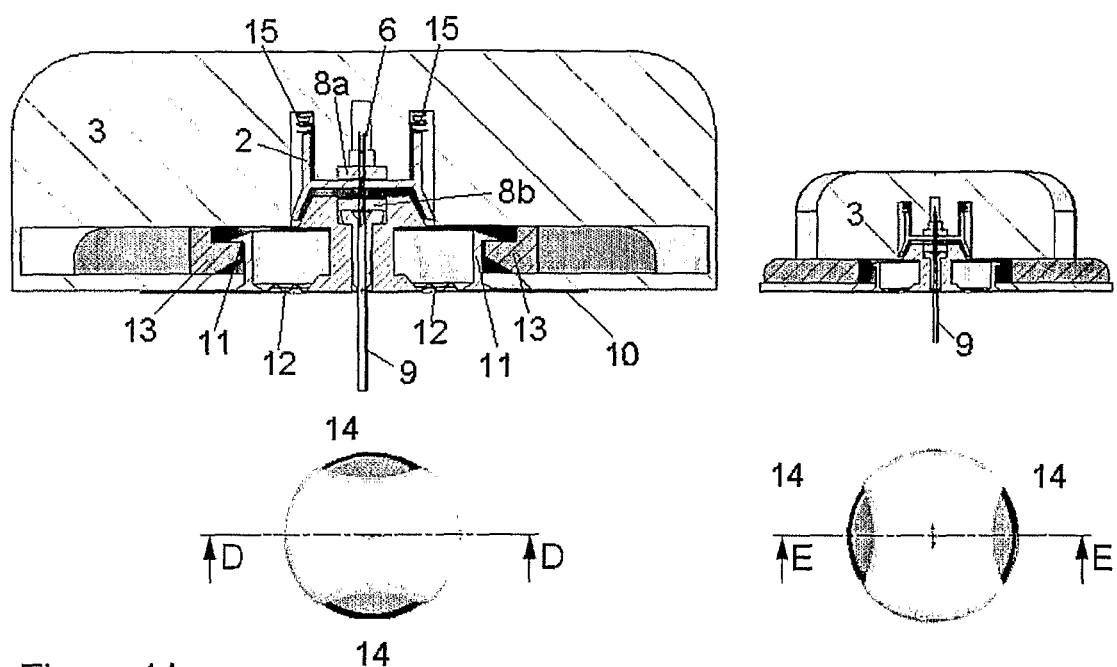
FIG. 11 shows a third embodiment of a delivery device according to the invention in a connected state, and in this embodiment the delivery part is placed on top of the injection part.

FIG. 11 illustrates an embodiment where the delivery part 3, 4 is placed on top of the injection part. In this embodiment the delivery part is fastened releasably to a portion of the base part 10 which surrounds the cannula part 1. The flexible portion 12 of the base plate 10 placed around the injection part is formed as a circular folded material which is either the same material as the central part of the injection part in a thinner form or of a different material of a more soft or flexible nature. In FIG. 11 the delivery part 3, 4 and the injection part are joined together as they would be when the device is in use and a connection which allows for fluid to flow from the reservoir to the cannula 9 is formed. The left and the right versions show views of two different cuts along the lines D-D and E-E respectively at perpendicular angles through the device. In this embodiment the objects 11 for fastening of the delivery part 3, 4 to the injection part are formed as circular profiles standing upright from the base part 10 and having an outward projection which objects 11 fit with corresponding projections 13 on the delivery part. When the delivery part 3, 4 is to be fastened to the cannula part 1 two handle portions 14 are pushed together which makes the corresponding projection move outwards and allow the injection part to enter the central opening in the delivery part 3, 4. When the user let go of the handle portions 14 the corresponding parts return to the more central position and locks the cannula part 1 to the central opening of the delivery part 3, 4.

The delivery part 3, 4 is combined with a connector 2; the connector 2 has a through-going connector needle 6 and is influenced by a spring 15. When the user pushes the delivery part 3, 4 towards the injection part, the spring 15 is compressed and the through-going connector needle 6 is forced through a septum 8 protecting the content of the reservoir from being infected with micro organisms. At the same time or just before or afterwards the connector needle 6 will also be forced through a septum 7 protecting the access to the cannula 9 thereby forming a fluid connection between the not shown reservoir and the cannula 9. By choosing convenient materials for the spring 15, the septum 8 and other materials being in contact with the connector 2, it should be assured that there exists a flexible connection between the connector 2 and the delivery part 3, 4. Preferably the connector 2 is fastened to the spring 15 while the movement from one position to another is guided by the walls of the central extension of the delivery part 3, 4, and the septum 8 is made of a material which is adequately soft to assure that the connector 2 is flexibly connected to the delivery part 3, 4 when the device is in a connected state. In this embodiment the connector 2 does not have to be fastened to neither the delivery part 3, 4 nor the injector part 1, the connector 2 can be a separate unit which functions as an independent interface or it can be integrated with either the delivery part 3, 4 or the injection part.

Figure 12:
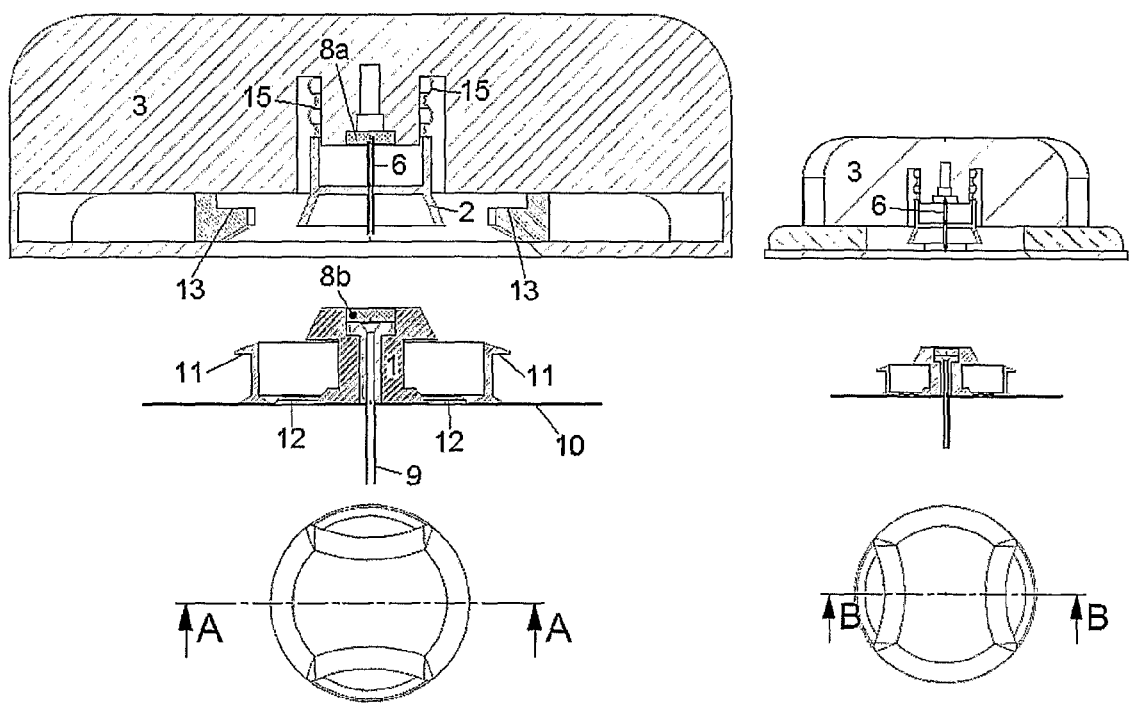
FIG. 12 shows the third embodiment of the device in a separated state.

In FIG. 12 the embodiment of FIG. 11 is shown in a state where the injection part is separated from the delivery part 3, 4 which leaves the spring 15 in a relaxed and extended state. In this state the through-going connector needle 6 has neither penetrated the septum 8 of the delivery part 3, 4 or the septum 7 of the cannula part 1.

Figure 13:
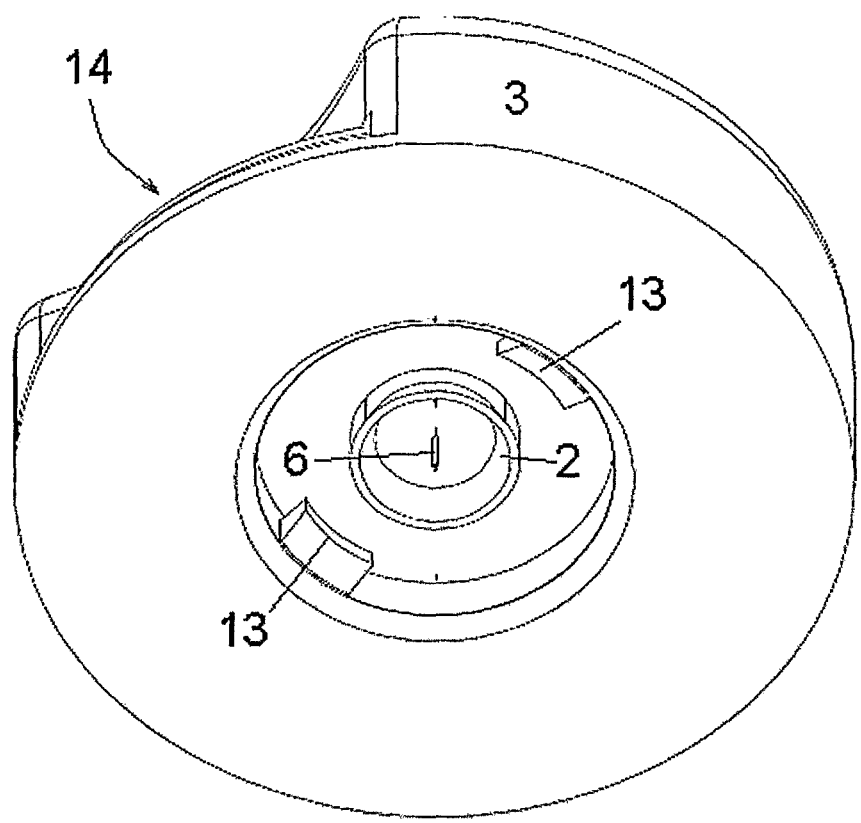
FIG. 13 shows the two parts of the third embodiment from the upper and lower side, respectively.
Figure 13:
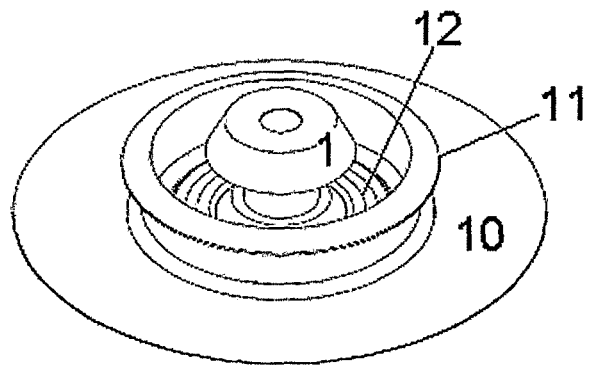

FIG. 13 shows the embodiment of FIGS. 11 and 12 in a three dimensional form. The delivery part 3, 4 and the injection part 1 joined to the base part 10 are shown from the sides where the two parts correspond to each other when joined.

The embodiment shown in FIG. 11-13 can be inserted with an inserter of the type known from PCT application DK02/00640 filed on Sep. 27, 2002. After insertion of the injection part, the user fastened the base part 10 to the skin. With the injection part in position the user can then fastened the delivery part comprising at least one reservoir and transferring means e.g. in the form of a pump to the injection part 1. If the connector 2 has the form of a separate interface the connector should be placed before the delivery part 3, 4 is fastened to the injection part and the connector will then provide for a proper fitting between the chosen injection part and the chosen delivery part 3, 4.

When introducing the flexible areas as described in FIGS. 1-13 and as claimed it will be possible to move the releasable delivery part 3, 4 in all dimensions within certain boundaries defined by the size of the used parts as it will be possible to pull, push, lift and move the delivery part 3, 4 side wards without influencing the cannula 9 and disturbing the insertion site which would normally result in discomfort to the patient.

All the embodiments containing is fastened to the patients skin and this is normally done by applying a mounting pad adhered to the proximal side of the base part 10 or to the proximal side of the infusion part if the embodiment is not provided with a base part 10. The adhering of the mounting pad to the base part 10 or infusion part 1 can include glue, Velcro, molding etc.

Figure 14:
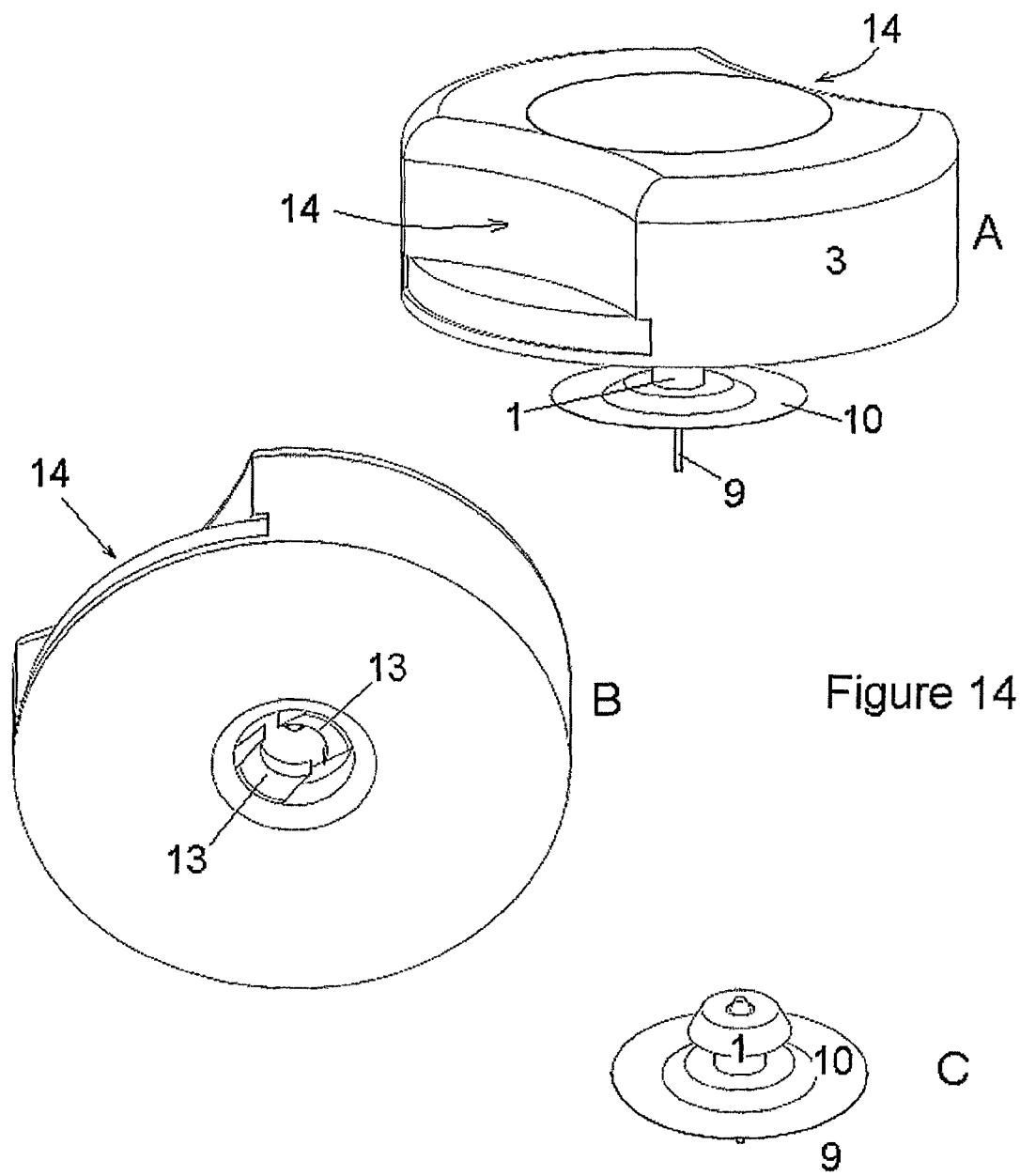
FIG. 14 shows a fourth embodiment of the delivery device according to the invention. "A" shows the delivery part with the injection part prepared to be connected with the delivery part seen from the side, "B" shows the delivery part from beyond and "C" shows the injection part seen from above.

FIG. 14 shows an embodiment of the invention according to which it is possible to assure a fluid tight transferal of fluid from the reservoir in the delivery part 3, 4 to the cannula 9 of the cannula part 1 and thereby to the patient.

In FIG. 14 "A" shows the device comprising both the delivery part 3, 4 and the injection part including the cannula part 1 seen from the side in a three dimensional form, "B" shows the delivery part 3, 4 from below in a three dimensional form and "C" shows the injection part seen from above in a three dimensional form.

Figure 15:
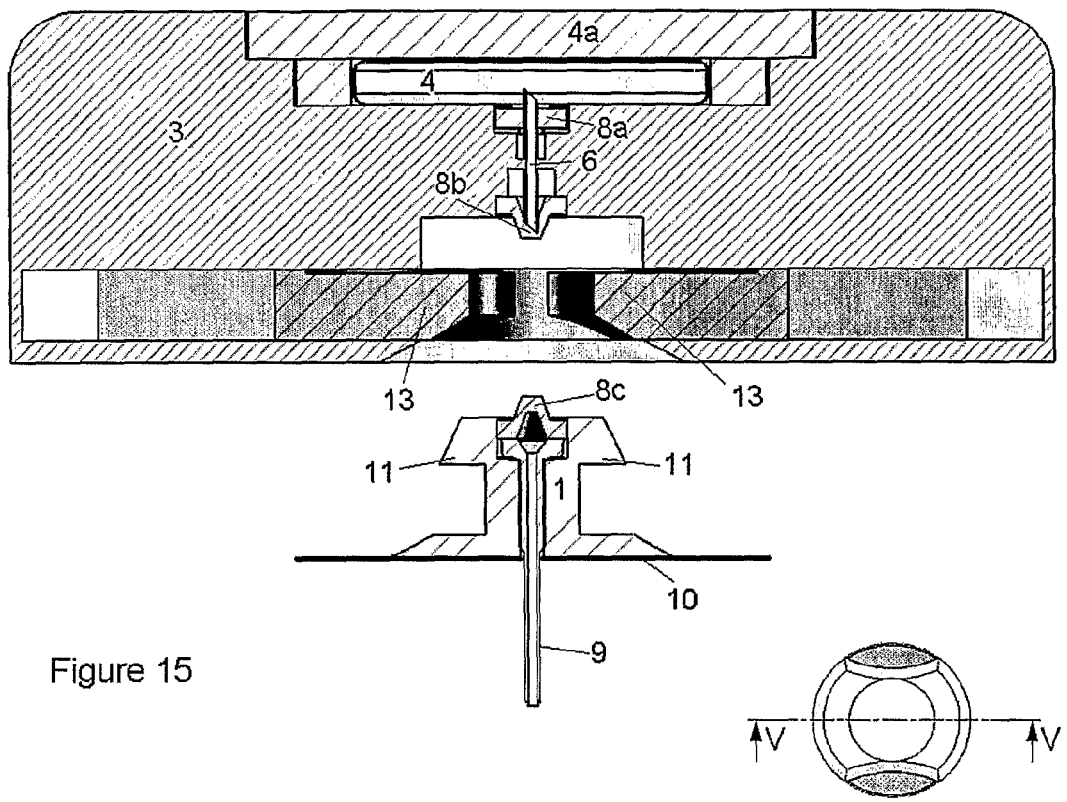
FIG. 15 shows the fourth embodiment seen from the side (line V-V) in a separated state.

FIG. 15 shows the same embodiment as in FIG. 14 and is a side view of the cut illustrated by the line V-V. In FIG. 15 the delivery part 3, 4 and the injection part are separated and the connector needle 6 is protected by a downward septum 8b preventing bacteria to enter the reservoir from this end. The septum 8a protecting the entrance of the reservoir is penetrated by the other end of the connector needle 6. In FIG. 15 the reservoir 4 is shown positioned above the connector needle 6 and above the reservoir 4 is a reservoir lid 4a shown. The reservoir lid 4a can be removed when e.g. an ampoule constituting the reservoir 4 has to be changed. In this embodiment the reservoir 4 has flexible walls and is surrounded by a ring 16 with which it is possible to reduce the volume of the reservoir and thereby pump fluid from the reservoir 4 to the patient. In this embodiment the cannula part 1 is also provided with an entrance septum 7 and with objects 11 for fastening of the delivery part 3, 4 to the injection part formed as a circular profile standing upright from the base plate 10 and being integrated with the outer surface of the housing of the injection part 1. The outward projection of the objects 11 fit with corresponding projections 13 on the delivery part 3, 4. When the delivery part 3, 4 is to be fastened to the injection part the two handle portions 14 are pushed together forcing the corresponding projections 13 outwards and allowing the injection part to enter the central opening in the delivery part 3, 4. When the user let go of the handle portions 14 the corresponding parts 13 return to the more central position and locks the injection part to the central opening of the delivery part 3, 4. In this embodiment the cannula part 1 can be made of a non-rigid material in order to provide a flexible part whose increased flexibility assures that the movements of the delivery part 3, 4 is not transferred to the cannula 9.

Figure 16:
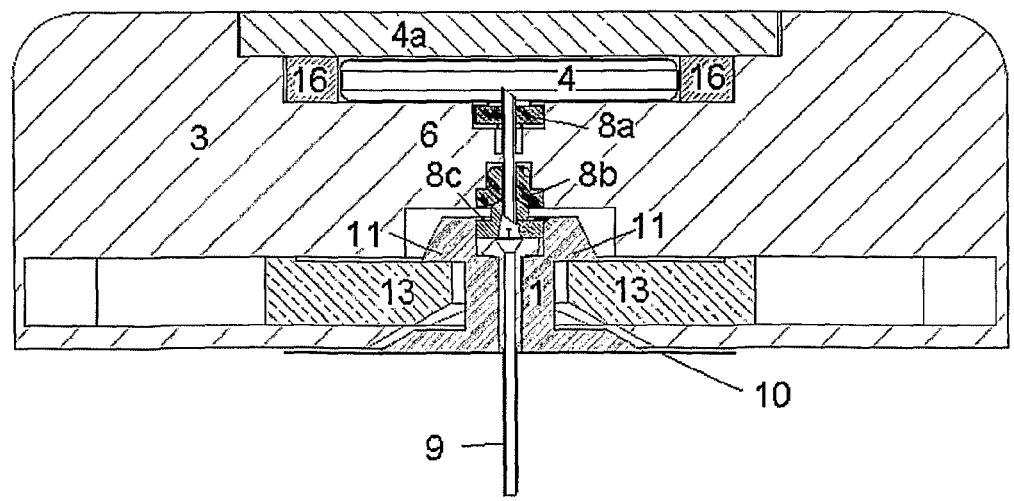
FIG. 16 shows the fourth embodiment seen from the side (line V-V) in a connected state.

FIG. 16 shows the same embodiment as in FIGS. 14 and 15 but in FIG. 16 the delivery part 3, 4 and the injection part are joined together as they would be during use. In this position the connector needle 6 has penetrated all three septa 8a, 8b and 7 and has created a fluid connection between the reservoir 4 and the injection part.

Figure 17:
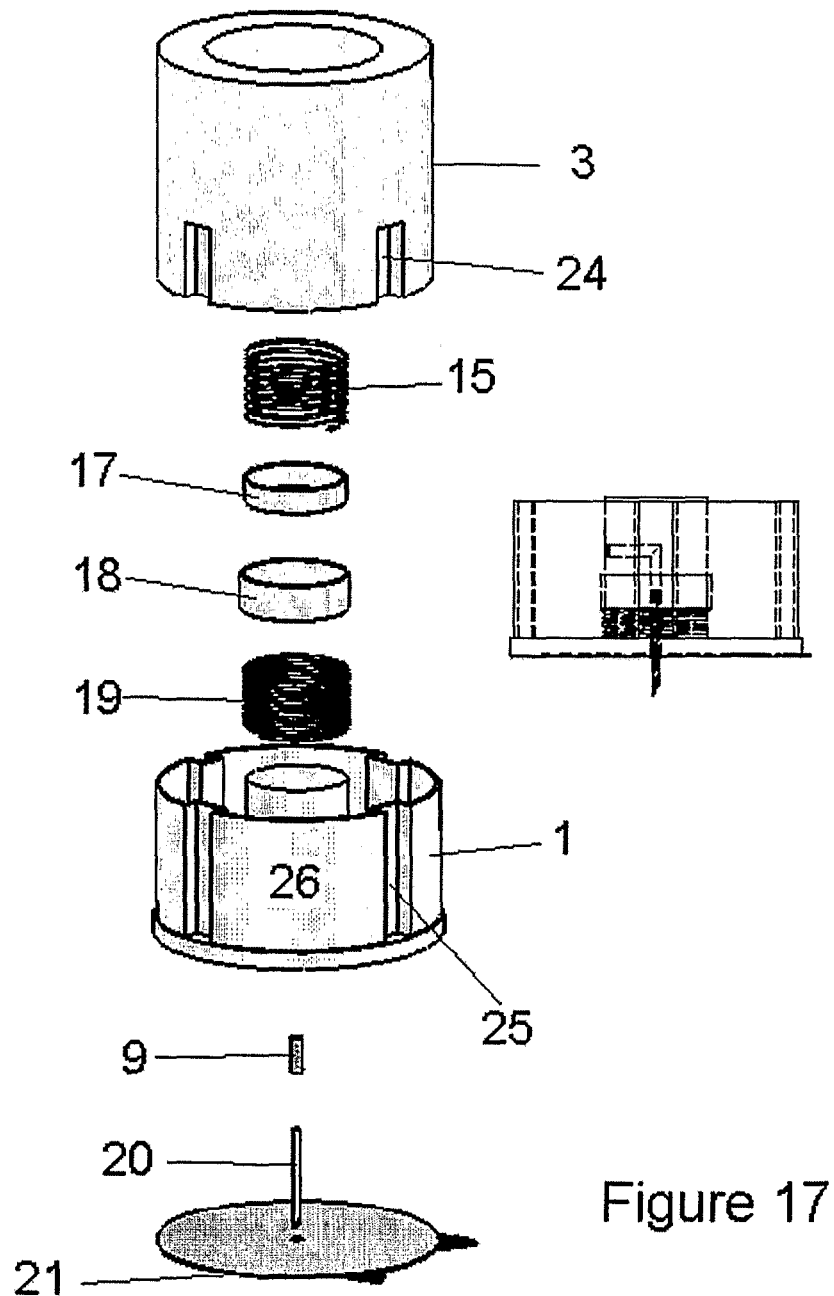
FIG. 17 shows a fifth embodiment of the delivery device according to the invention having a fluid tight lock between the delivery part and the injection part.

FIG. 17 shows an exploded view of an embodiment of a device comprising a second fluid tight connection between the reservoir of the delivery part 3, 4 and the injection part. This embodiment comprises a delivery part comprising a pump and a reservoir, a first spring 15, an upper packing 17, a lower packing 18, a second spring 19, and an injection part comprising a cannula part 1 including a cannula 9, an insertion needle 20, an outer wall 26 and a mounting pad 21. Further the outward surface of the delivery part, the cover or house 3, is provided with grooves 24 and the outward surface of the outer wall 26 of the injection part is provided with corresponding tongues 25.

Figures 18A, 18B:
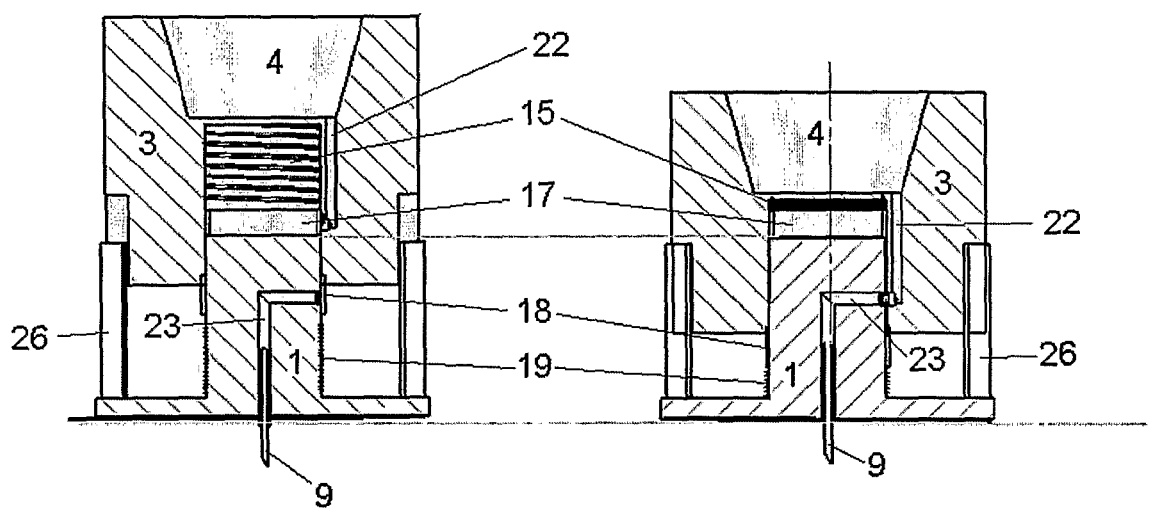
FIGS. 18A and 18B show an enlarged part of the fifth embodiment in two states; in the first state the device is closed for fluid flow, in the second state the device is open for fluid flow.

In FIG. 18 it is shown how the individual parts of the embodiment in FIG. 17 works together. In this figure the insides of the injection part and the delivery part 3, 4 are illustrated. In FIG. 18 is shown a possible placement of the reservoir 4 in the delivery part 3 and an outlet pipe 22 from the reservoir 4. At the outlet end, in FIG. 18 the lowest end, the outlet pipe 22 is provided with a sideway directed opening and a packing which packing assures fluid tight contact between the wall of the central part of the cannula part 1 and the outlet of the outlet pipe 22. The inside of the cannula part 1 comprises a through-going fluid path 23 with an inlet opening sideways through the upright wall of the central part of the injection part. In order to provide a flexible part the cannula part 1 and the outer wall 26 can be made of a resilient or non-rigid material. The degree of elasticity which is desired will depend on the physical appearance of the delivery device i.e. size and weight.

In a first position the delivery part comprising the reservoir 4 and the pump is retracted from the injection part, the first spring 15 is extended and the outlet from the outlet pipe 22 is blocked by the wall of the central part of the injection part i.e. the cannula part 1. The lower packing 18 is in a high position where it blocks the inlet of the fluid path 23 and the second spring 19 is extended.

In a second position the delivery part 3, 4 is pushed towards the injection part and both the first spring 15 and the second spring 19 are compressed. The lower packing 18, which in the first position functions as a barrier for bacteria, is pushed down by the lower edge of the delivery part 3, 4 and thereby opens the inlet of the fluid path 23. When the tongues 25 of the injection part touch the upper side of the grooves 24 of the delivery part 3, 4 the downward movement of the delivery part stop and in this position the opening of the outlet pipe 22 corresponds to the inlet of the fluid path 23.

Figure 19:
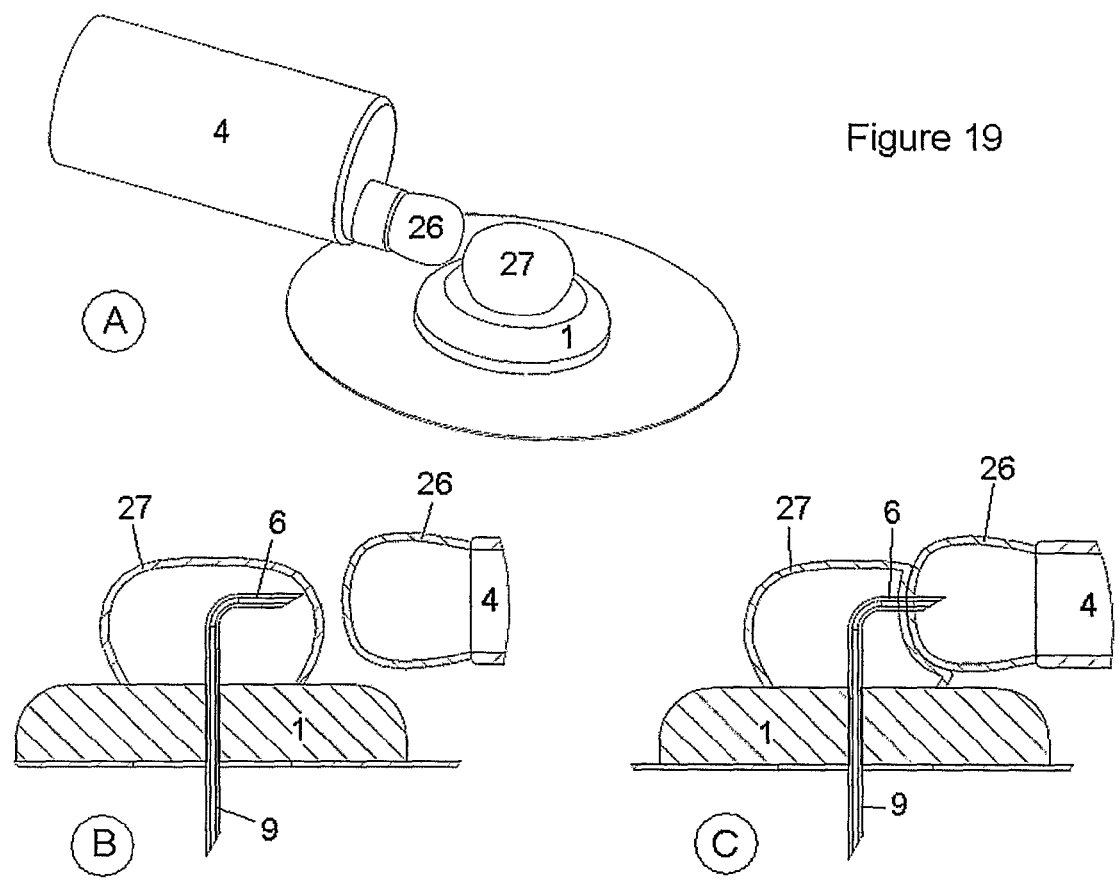
FIG. 19 shows another embodiment ensuring fluid tight transferal of fluid from the delivery part to the injection part.
Figure 22:
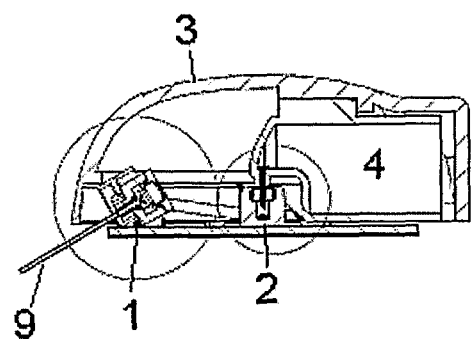
FIG. 22 shows a cut through view of the sixth embodiment in the joined state of FIG. 21.
Figure 23:
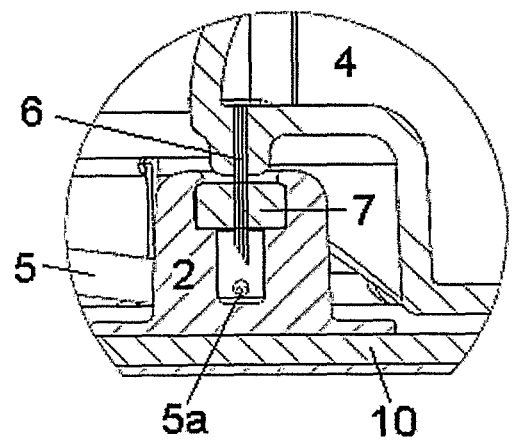
FIG. 23 shows an enlargement of the connector part of FIG. 22.
Figure 24:
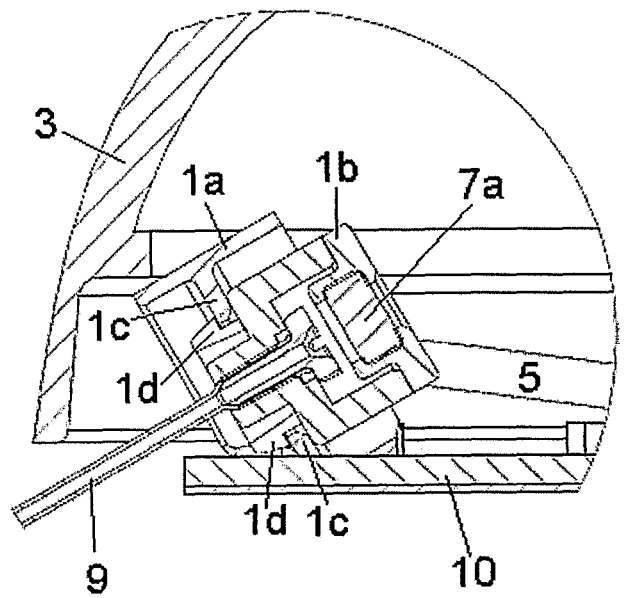
FIG. 24 shows an enlargement of the injector part of FIG. 22.
Figure 25:
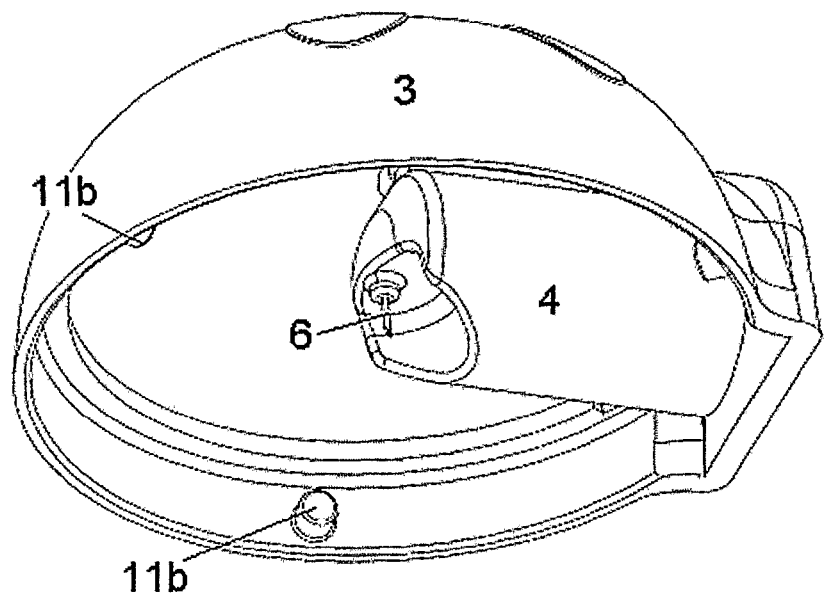
FIG. 25 shows a view from below of the delivery part of the sixth embodiment.
Figure 26:
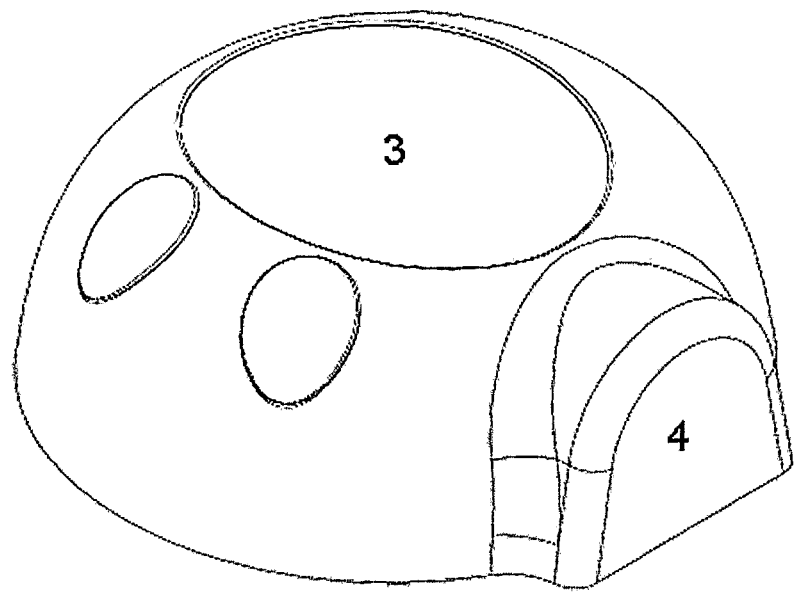
FIG. 26 shows a seventh embodiment having a base part equipped with a central combined connector and injection part.
Figure 26:
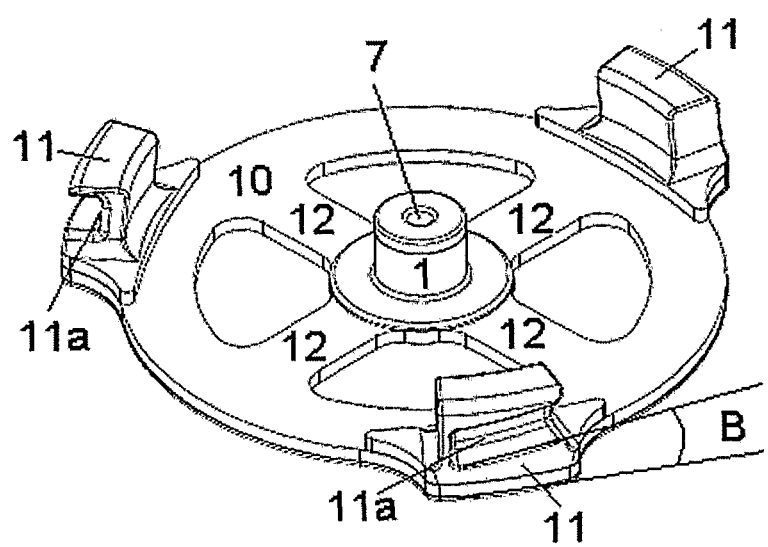
Figure 29:
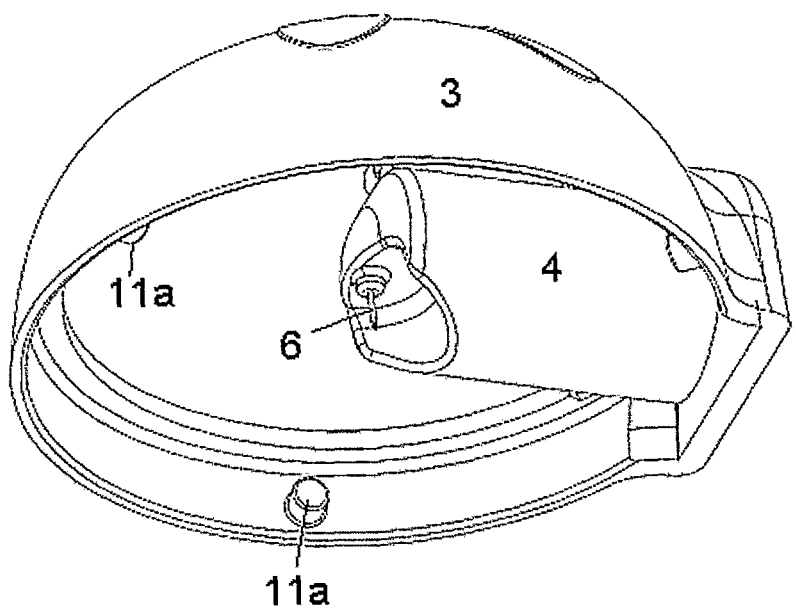
FIG. 29 shows a view from below of the delivery part of the seventh embodiment.

FIG. 19 shows an embodiment of a fluid tight connection between the reservoir and the injection part. In this embodiment the flexible part can be provided by elastic "bubbles" 26 and 27. This device comprises a delivery part 3, 4 e.g. as shown in FIG. 1-10 but only the reservoir 4 is shown in FIG. 19. The device is constructed of a reservoir where the outlet is covered by a bubble shaped deformable membrane 26; this membrane prevents that micro organisms access the reservoir when the delivery part is not joined to the injection part 1. That the membrane is bubble shaped means that the membrane not has flat inner and outer surfaces but has convex inner and outer surfaces, and that the membrane does not only cover the tip of the connector needle 6 but covers a larger part of the connector needle 6. The inlet of the injection part 1 is also covered by a deformable bubble shaped membrane 27. In this embodiment the connector needle 6 is fastened to the injection part 1 but the connector needle 6 could also be fastened to the delivery part 3, 4, if the connector needle 6 is fastened to the delivery part it is necessary to provide the combined device with two needles: a connector needle 6 and a cannula 9. If the device is provided with a connector needle 6 separate from the cannula 9 it is possible to use a soft cannula.

FIG. 19A shows a three dimensional view of the device in a state where the delivery part 3, 4 and the injection part 1 are separated and fluid can not flow between the two parts. FIG. 19B shows the same state as FIG. 19A but seen from a vertical cut through the device. In FIG. 19C the delivery part 3, 4 and the injection part 1 has been pushed together and the fluid of the reservoir 4 can now flow through the injection part 1 and the cannula 9 to the patient. When the two membranes are pushed together membranes are deformed and the pointy connector needle 6 penetrates both membranes and forms a fluid connection, it is possible to form each of the bubble shaped membranes 26 and 27 with a varying hardness in order to control where it is desirable to penetrate the membranes by using the varying hardness to shape a base for the least deformable membrane when it is pushed against the most deformable membrane.

The membranes 26 and 27 can be made of silicone or polyurethane (PUR) or other soft polymers which can be penetrated by a needle but not by micro organisms.

The connector needle 6 is made of a relatively hard material such as metal or a hard polymer, "a relatively hard material" means that the material should at least have the strength, i.e. be hard enough, to penetrate the membranes 26 and 27.

In the embodiment of FIGS. 19A, B and C the connector needle 6 is one end of a single needle which at the other end functions as the cannula 9. When the connector needle 6 and the cannula is formed as one needle it will normally be made of metal or hard polymer but it can also be made of e.g. a polymer which is hardened in the connector end and unhardened and soft in the cannula end. Also the single needle can be composed of two different materials, a hard material for the connector end and a relatively soft material for the cannula end.

It is also possible to separate the connector needle 6 and the cannula 9 and produce the device according to the invention with two needles. The injector part 1 can then be provided with a commonly known soft cannula which cannula can be inserted by the help of an insertion needle attached to a separate inserter, and the connector needle 6 is made of a hard material and fastened to either the injector part 1 or the delivery part 3, 4.

In this embodiment the single needle is bend, i.e. the connector needle 6 points in a direction parallel to the patients skin while the cannula 9 points in a direction perpendicular to the patients skin. According to the present invention the connector needle 6 can point in any direction parallel or away from the patient and the cannula 9 can point in any direction according to which the cannula can be inserted into the patient's skin.

The device according to the invention can be used in connection with all kinds of medicaments and all kind of conditions where patients can benefit from a continuous intake of a drug product; preferably it is the intention to provide patients suffering from diabetes with a secure and easy-to-handle device which can provide the patient with continuously regulated doses of insulin.

In one embodiment the reservoir is divided into several separate chambers where each chamber can be provided with different drug products or e.g. an active drug substance in one chamber and a solvent in another chamber, the different chambers can contain drugs of different concentrations or drugs with different active substances.

FIG. 20-25 show an embodiment of the invention where the connector 2 has been placed in a central position of the base plate 10 and the cannula part 1b is fastened to a peripheral part of the base plate 10. The peripheral placement of the cannula part 1b makes it possible for the user to observe the injection site. Further the cannula part of this embodiment is arranged in such a way that the cannula 9 is to be injected at an angle A deviating from 90° in relation to the distal surface of the base plate 10, normally the angle A will be between 110° and 170° where the distal surface of the base plate 10 form one side of the angle and the inserted cannula 9 form the other side of the angle.

In this embodiment the flexible part is integrated in the base plate 10 by providing a flexible portion 12 constructed from the base plate 10 and formed like four spokes in a wheel. It is possible to vary the elasticity of the flexible portions 12 by varying the width of the portions 12, the thickness of the base plate material 10 or the number of portions 12 (spokes).

The cannula part is a two-part unit comprising a first part 1a which is fastened unreleasably to the base plate 10 and a second part 1b comprising a body providing a through-going opening leading liquid to the cannula 9 which cannula 9 extends at the proximal side of the base plate 10 after insertion. The cannula part 1a, 1b partly forms the fluid connection between the patient and the reservoir 4.

It is possible to position this embodiment on the skin of the patient applying at least two different methods. According to one method the base plate 10 comprising the first part 1a is first positioned on the skin of the patient and thereafter the cannula-holding second part 1b of the cannula part 1 is injected e.g. with an especially adapted inserter, this method makes it possible for the user to exercise more care when positioning the base plate 10 which is normally equipped with an adhesive pad. According to a second method the base plate 10 comprising both the first part 1a and the cannula-holding second part 1b is injected all together with an inserter adapted to hold the entire device, this method comprises one less mounting step compared to the earlier described method.

In this embodiment the first part 1a is provided with inward projecting parts 1c and the second part 1b is provided with outward projecting, pivotably fastened hooks 1d. When the second part 1b is positioned in the first part 1a, the outward projecting hooks 1d are first pushed outward by the inward projecting parts 1c and after having passed the projecting parts 1c, the projecting hooks 1d return to their original position and locks the first part 1a inside the second part 1a.

The base plate 10 is provided with three upright positioned objects 11 for fastening of the delivery part 3, 4 to the base plate 10; the numbers of objects 11 are optional and the objects 11 can be either molded together with the base plate 10 or fastened to the base plate 10 after the base plate 10 has been formed e.g. by gluing or welding. The objects 11 are provided with sliding grooves 11a which sliding grooves 11a define the direction in which to move the delivery part 3, 4 when securing the delivery part 3, 4 to the base plate 10. The sliding grooves 11a correspond to protruding parts 1b on the delivery part 3, 4. In this embodiment the sliding grooves 11a are not parallel with the surface of the base plate 10 but differs in an angle B: $0°<B<45°$ where one side of the angle B is the distal surface of the base plate 10 and the other side of the angle B is the distal edge of the sliding grooves 11a. The angle B—together with the round shape of the delivery part 3, 4 and the central position of the connector 2—makes it possible to screw the delivery part 3, 4 on to the base plate 10.

The connector 2 is constructed of a molded body fastened unreleasably to the base plate 10 and provided with an interior compartment to which access is protected by a septum 7. The septum 7 is penetrated by the connector needle 6 when the delivery part 3, 4 is fastened to the base plate 10. From the lower part of the interior compartment and opening 5a allows fluid to enter into the flexible tube 5 and pass onto the patient through the cannula 9. The flexible tube 5 is connected to the first part 1a of the injection part and when the second part 1b of the cannula part is positioned in the first part 1a a fluid path is created from the flexible tube 5 to the cannula 9.

The reservoir 4 of the shown embodiment will normally hold between 0.5-3 ml of fluid for transferal to the patient.

FIG. 26-29 shows an embodiment of the invention where the connector needle 6 is inserted directly into the injection part i.e. there is no separate connection part. The cannula part 1 is placed in a central position of the base plate 10 and therefore it is not possible for the user to observe the injection site.

In this embodiment the flexible portion 12 is also constructed from the base plate 10 and formed like four spokes in a wheel.

The cannula part 1 is one unit comprising a molded body with an interior compartment. The interior compartment can be accessed through the protective seal 7 by the connector needle 6 when the delivery part including the reservoir 4 is placed in correct position. From the interior compartment fluid can be channeled out through the cannula 9.

The base plate 10 is like the embodiment of FIG. 20-25 provided with three upright positioned objects 11 for fastening of the delivery part 3, 4 to the base plate 10; the numbers of objects 11 are optional.

In the embodiment of FIG. 26-29 the base plate 10 is placed on the skin of the patient simultaneously with injection of the cannula 9 of the injection part and the cannula 9 is inserted in a 90° angle. In order to insert the device an inserter of the type shown in EP 1 429 826 can be used.

Figure 30:
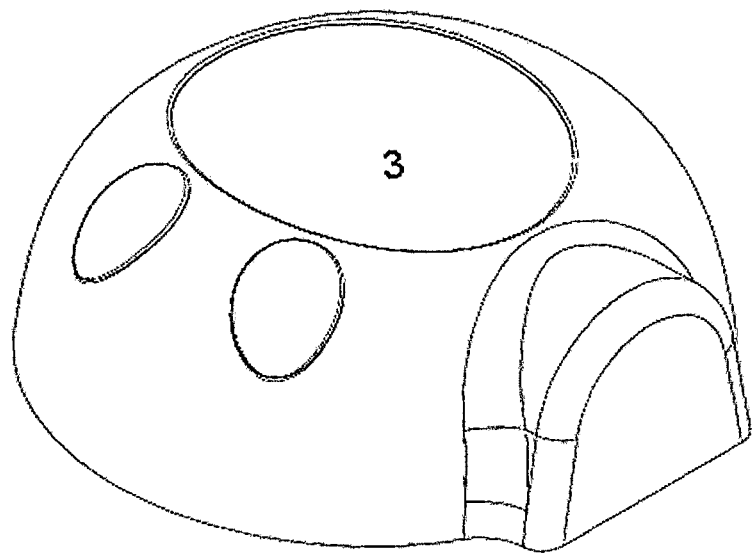
FIG. 30 shows an eighth embodiment having a base part equipped with a central combined connector and injection part where the combined part is divided into to units.
Figure 30:
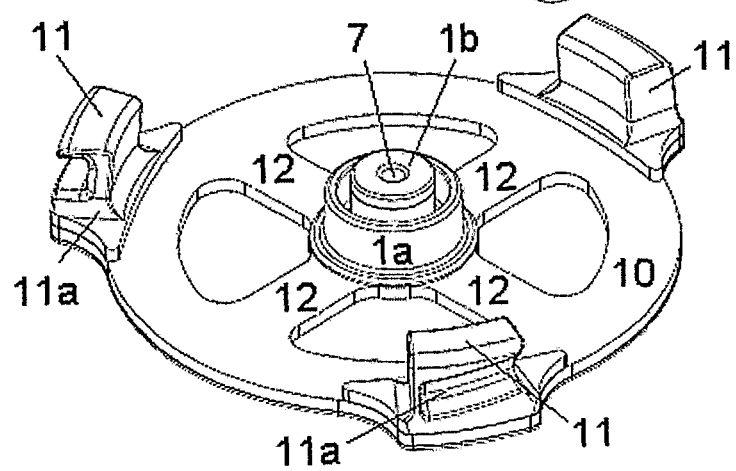
Figure 31:
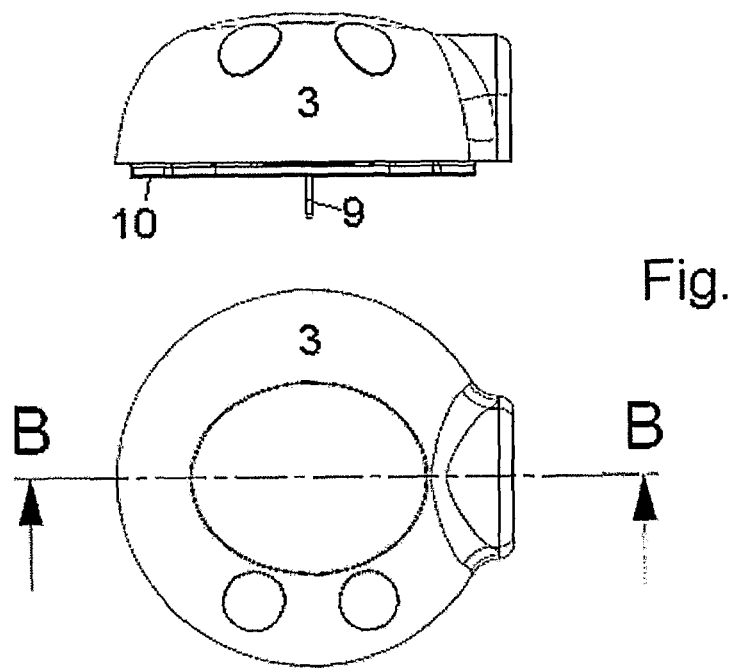
FIG. 31 shows the delivery device and the base part of the eighth embodiment in a joined state from above and from the side.
Figure 32:
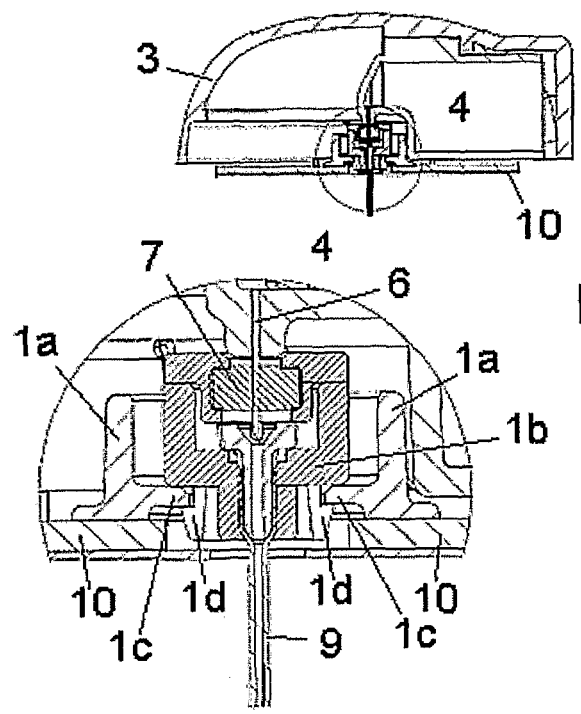
FIG. 32 shows a cut through view of the eighth embodiment in the joined state of FIG. 31 and an enlargement of the combined connector/injection part.
Figure 33:
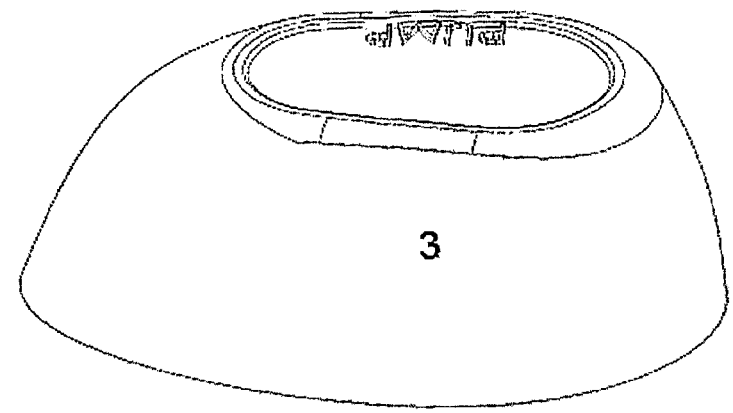
FIG. 33 shows a ninth embodiment having an oval base part equipped with a central connector and peripheral injection part.
Figure 34:
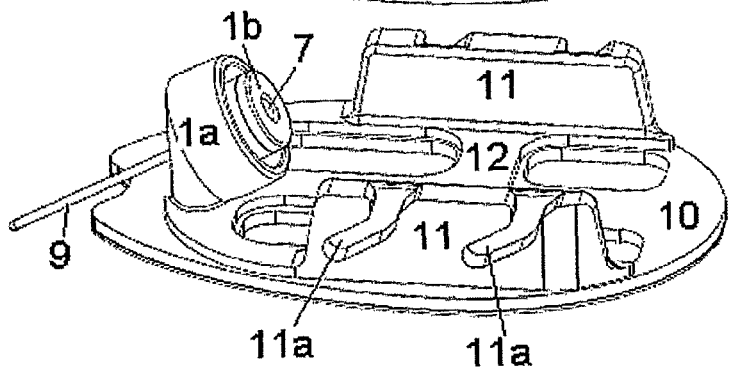
FIG. 34 shows the delivery device and the base part of the ninth embodiment in a separated state from below and the reservoir and the base part from the side.
Figure 34:
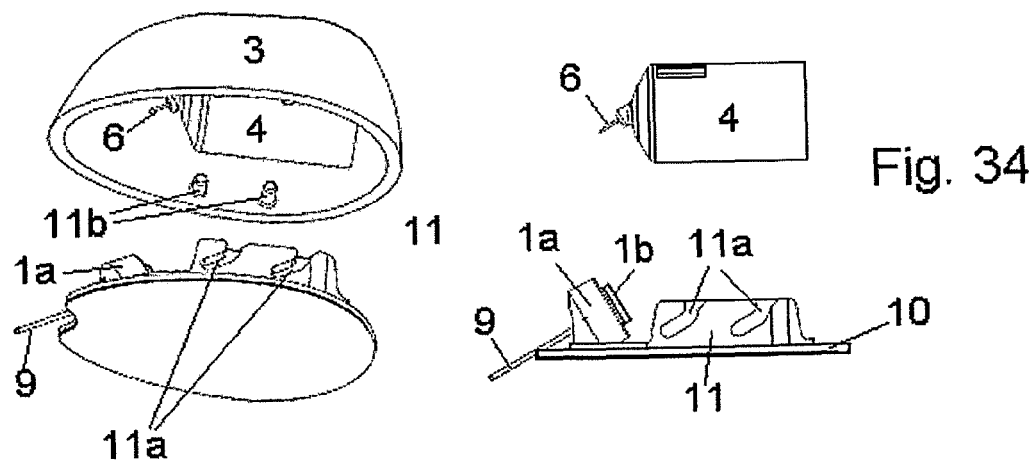
Figure 35:
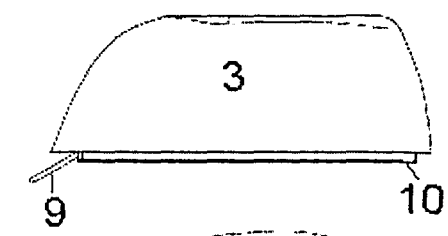
FIG. 35 shows the delivery device and the base part of the ninth embodiment in a joined state from the side and from above.
Figure 35:
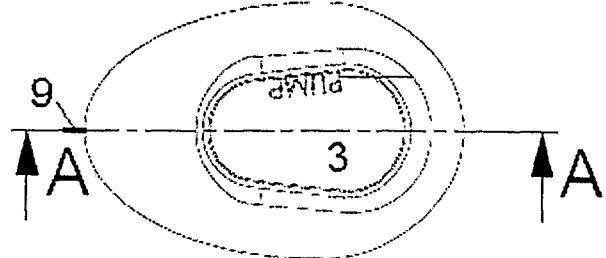
Figure 36:
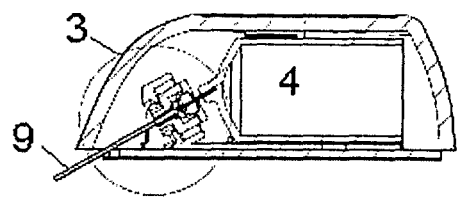
FIG. 36 shows a cut through view of the ninth embodiment in the joined state of FIG. 35 and an enlargement of the injection part.
Figure 36:
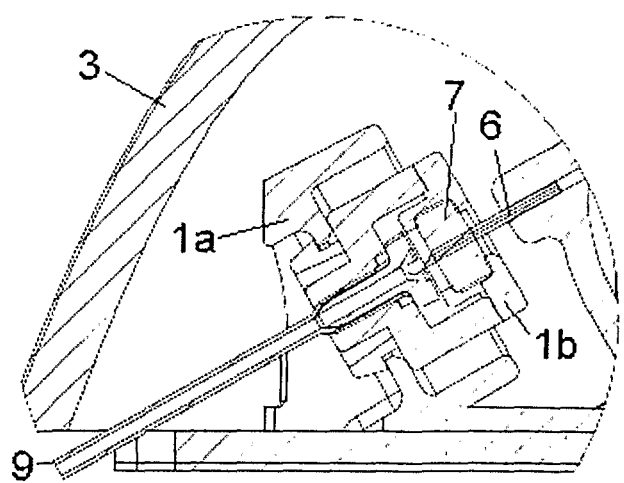

FIG. 30-32 shows an embodiment of the invention which as the embodiment of FIG. 26-29 is without a separate connector. The cannula part 1a, 1b is placed in a central position of the base plate 10 and therefore it is not possible for the user to observe the injection site.

In this embodiment the flexible portion 12 is also constructed from the base plate 10 and formed like four spokes in a wheel.

The cannula part is a two-part unit comprising a first part 1a which is fastened unreleasably to the base plate 10 and a second part 1b comprising the cannula 9. According to this embodiment the base plate 10 is positioned on the skin of the patient first and then the cannula-holding part 1b of the cannula part is injected in the allocated position. Like the embodiment shown in FIG. 20-25 the first part 1a of this embodiment is provided with inward projecting parts 1c and the second part 1b is provided with outward projecting and pivotably fastened hooks 1d which corresponding parts can lock the second part 1b in the desired position.

FIG. 33-36 shows an embodiment of the invention where the cannula part 1 is fastened to a peripheral part of the base plate 10 from which position it is possible to perform an angled injection and thereby making it possible for the user to observe the injection site. In this embodiment the cannula part is of the two-part type comprising a first part 1a which is fastened unreleasably to the base plate 10 and a second part 1b comprising the cannula 9. The first part 1a is provided with inward projecting parts 1c and the second part 1b is provided with outward projecting and pivotably fastened hooks 1d.

The flexible portion 12 of this embodiment is also constructed from the base plate 10 but here the flexible portion 12 is formed like a lattice. According to this embodiment it is also possible to vary the flexibility of the flexible portions 12 by varying the width of the portions 12, the thickness of the base plate material 10 or the number of portions i.e. bars 12.

The base plate 10 is provided with two upright positioned objects 11 for fastening of the delivery part 3, 4 to the base plate 10; the numbers of objects 11 are optional and the objects 11 can be either molded together with the base plate 10 or fastened to the base plate 10 after the base plate 10 has been formed e.g. by gluing or welding. The objects 11 are provided with sliding grooves 11a which sliding grooves 11a define the direction in which to move the delivery part 3, 4 when securing the delivery part 3, 4 to the base plate 10. In this embodiment each object 11 is provided with two sliding grooves 11a, and each sliding groove 11a is inclined in an angle B: 0°<B<90°. The sliding grooves 11a correspond to protruding parts 11b on the delivery part 3, 4. The interaction between the sliding grooves 11a of the base plate 10 and the protruding parts 11b of the delivery part 3 assures correct insertion of the connector needle 6 through the protective seal 7 of the injection part 1b as the delivery part 3 moves along a well defined path during fastening to the base plate 10.

Generally when the cannula part 1 is constructed of a two-part unit 1a, 1b the method for fastening the device to the skin of the patient will comprise the following step:

If the base plate 10 is provided with an adhesive surface e.g. unreleasably combined to an adhesive pad, the adherent side of the base plate 10 is exposed e.g. by removing a release liner, the base plate 10 comprising a part of the injection part 1a is positioned on the skin of the patient, a second part of the injection part 1b is inserted into the position defined by the first part 1a, normally by use of an insertion device which could be a multi-use insertion device or a single-use insertion device, the delivery part 3 is positioned on top of the base plate 10.

Figure 37:
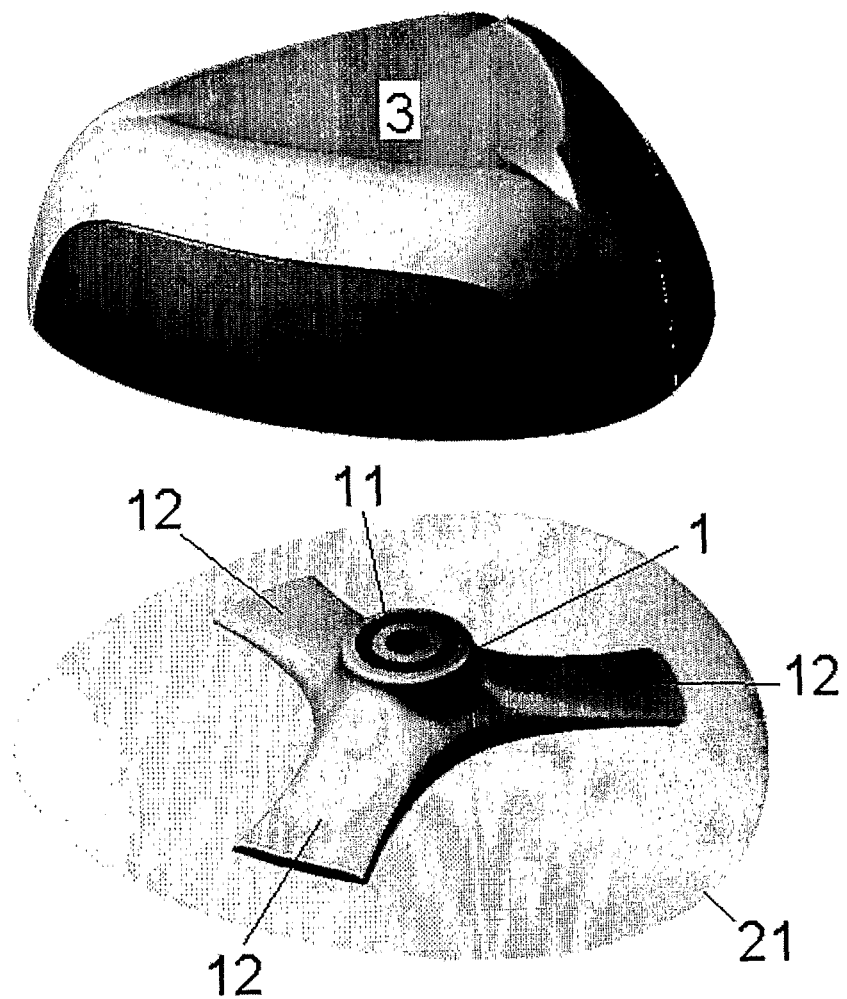
FIG. 37 shows a tenth embodiment of a device for delivering fluid comprising an injection part and a fluid delivery part, in FIG. 37 the two parts are shown in a separated state.
Figure 38:
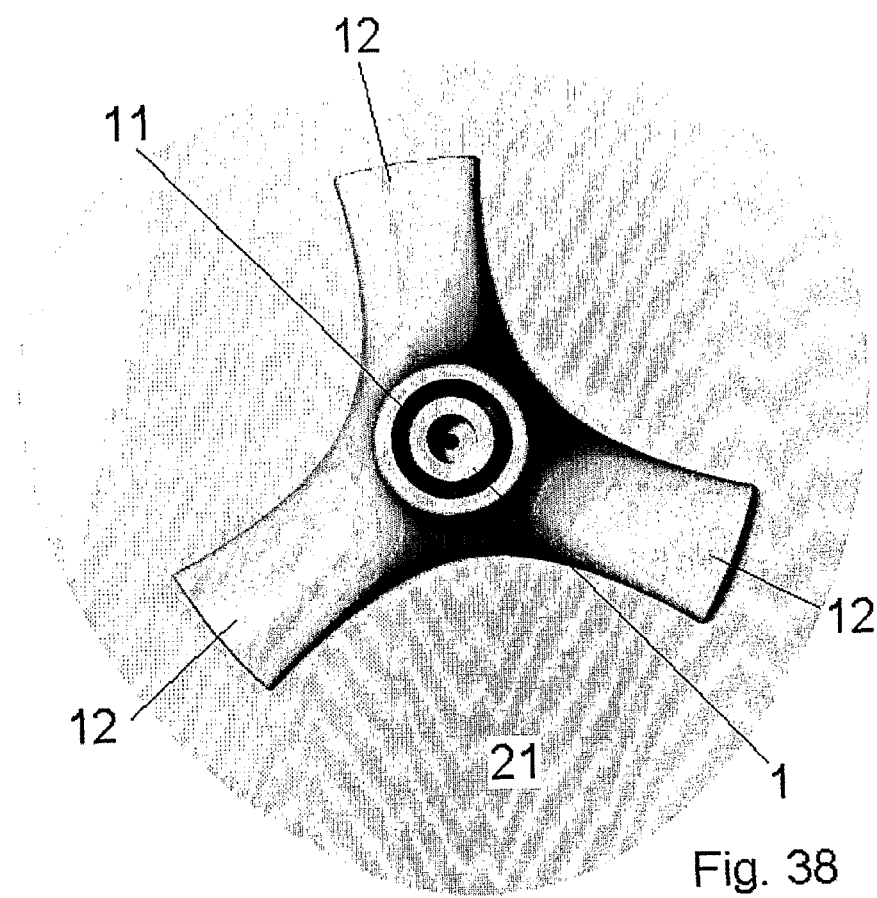
FIG. 38 shows the injection part of the tenth embodiment seen from above.

FIGS. 37-39 show an embodiment of the invention where the cannula part 1 has been placed in a central position of the base plate 10 of the injection part. The base plate 10 is in this embodiment constructed as three flexible portions 12 which are formed e.g. molded together with the cannula part 1 and unreleasably attached to the mounting pad 21 which pad also provides a certain degree of stability to the injection part. The portions 12 are relatively flat i.e. there height is smaller than there width and they are made of a material which provides the injection part with a structure of the desired flexibility.

It is possible to vary the elasticity of the flexible portions 12 by varying the number of the portions 12 and the width and thickness of the portions 12.

The cannula part 1 comprises a body providing a through-going opening leading liquid to a not shown cannula 9 which cannula 9 extends at the proximal side of the injection part after insertion, i.e. the cannula part 1 partly forms the fluid connection between the patient and the reservoir 4. The cannula part 1 is also provided with a round-going upright wall 11 which in this embodiment constitutes the fastening means for the delivery device 3.

The delivery part and the injection part of this embodiment are joined by just pressing the two parts together.

FIG. 40 shows another embodiment of the injection part without the mounting pad where the delivery part is fastened to the injection part both by turning the delivery part down on the central cannula part and by clicking it on to the peripheral upright objects 11. The peripheral objects 11 will secure the delivery part in a position close to the skin of the user.

In this embodiment the flexible portion 12 is constructed from the base plate 10 and formed like three spokes in a wheel.

The cannula part 1 is one unit comprising a molded body with an interior compartment. The interior compartment can e.g. be accessed through a protective seal by a connector needle when a delivery part including a house 3 and the reservoir 4 is placed in correct position.

The base plate 10 is like the embodiment of FIG. 20-25 provided with three upright positioned objects 11 for fastening of the delivery part 3, 4 to the base plate 10; and further the outside wall of the cannula part 1 is provided with sliding grooves 11a which sliding grooves 11a define the direction in which to move the delivery part 3, 4 when securing the delivery part 3, 4 to the base plate 10. The sliding grooves 11a correspond to protruding parts on the delivery part 3, 4. When the delivery part reaches the base plate 10 the upright peripheral parts 11 are pivoted outwards and the delivery part reaches its end position with a clicking sound as the upright peripheral parts 11 pivot back in upright position. The snap lock provided by the corporation between the delivery part and the peripheral parts 11 also keeps the device close to the skin of the user.

FIGS. 41a-b show different embodiments of the house 3 of the delivery part.

The invention claimed is:

1. A device for delivering fluid which before injection comprises three separate parts: an injection part, a cannula part and a fluid delivery part and after injection the device comprises two separable parts: an injection part and a fluid delivery part as the cannula part is attached to the injection part when inserted into a subcutaneous position;

the fluid delivery part comprising a reservoir, a pump and a housing, the injection part further comprises a base plate, the base plate comprises an adhesive portion for fixation of the base plate to the skin of the user, the base plate further comprising a connector for releasably connecting the fluid delivery part to the base plate such that the fluid delivery part is separable from the base plate during use, the connector extending from a distal side of the base plate, the base plate further comprising a surface on the distal side corresponding to an inserter device for the cannula part for attaching the cannula part to the injection part; and the cannula part is before injection placed in a separate inserter device and comprises a body and a cannula, the cannula is made of a soft material and configured to be inserted by an injection needle of the inserter device, the body providing a through-going opening configured to lead liquid to the cannula, the cannula part configured to be inserted into and attached to the base plate after the base plate has been positioned on the skin of the patient, the cannula part comprising a cannula part locking mechanism configured to attach the cannula part to the base plate independent of the fluid delivery part, the cannula extending past a proximal side of the base plate after injection of the cannula into a use position, wherein the device further comprises a flexible tube connecting the connector of the injection part at one end and the body of the cannula part at a second end to provide fluid communication between the reservoir and cannula.

2. A device according to claim 1, wherein the base plate is constructed either partially or completely from a flexible material.

3. A device according to claim 1, wherein the body of the cannula part is constructed either partially or completely from a flexible material.

4. A device according to claim 1, wherein the housing of the fluid delivery part also provides a housing for the injection part.

5. A device according to claim 1, wherein the cannula and the delivery part are not interconnected by non-flexible areas.

6. A device according to claim 1, wherein a fluid tight connection leading fluid from the reservoir to the cannula is formed when the delivery part and the injection part are joined together.

7. A device according to claim 6, comprising a sealing member configured to seal an opening of the reservoir to prevent access of micro organisms to the reservoir of the fluid delivery part during periods when the fluid delivery part and the injection part are separated.

8. A device according to claim 7, wherein the reservoir has two positions, a first position wherein an outlet from the reservoir is blocked with a first barrier which is not permeable for microorganisms and an inlet of the through-going opening in the cannula part is blocked with a second barrier which is not permeable for microorganisms, and a second position wherein an open fluid connection is formed between the reservoir and the through-going opening in the cannula part.

9. A device according to claim 8, wherein one or both of the barriers comprise a material which can be penetrated by a needle-like object where an opening formed in the material re-closes on retraction of the needle-like object.

10. A device according to claim 9, characterized in that the needle-like object is blunt.

11. A device according to claim 9, characterized in that the needle-like object is sharp-pointed.

12. A device according to claim 8, wherein one or both of the barriers comprise a hard surface which is moved forming an opening in an area positioned between an outlet of an outlet pipe and the inlet of the through-going fluid path.

13. A device according to claim 1, wherein the adhesive portion for fixation of the base plate to the skin of the user comprises a mounting pad adhered to the proximal side of the base plate or to a proximal side of the cannula part.

14. A device according to claim 1, wherein the base plate comprises a lattice with a peripheral coherent part and one or more bars interconnecting the peripheral part.

15. A device according to claim 14, wherein the base plate has a round or oval peripheral part and the bars have one end attached to the peripheral area and a second end attached to a central area.

16. A device according to claim 14 wherein the base plate has three or more bars.

17. A device according to claim 1, wherein the cannula comprises a cannula housing having a first end including solid walls and a protective seal protecting the entrance to the cannula.

18. A device according to claim 1, wherein the base plate comprises a first part of a cannula part configured to position a second part comprising the cannula.

19. A device according to claim 18, wherein the first part of the cannula part comprises the locking mechanism and the locking mechanism is configured to releasably lock the second part to the base plate in a desired position.

20. The device according to claim 1, wherein the base plate comprises a through opening, the cannula part comprising the cannula is insertable into the opening and allows for the injection needle of the inserter device to be removed from the injection part.

21. The device according to claim 1, wherein the cannula is inserted with the inserter device provided with a surface corresponding to the surface of the base plate and an inserter device connector, wherein connection of the inserter device connector to the base plate connector positions the inserter device so that the cannula including a body providing a fluid pathway to the cannula is inserted in correct relation to the base plate.

22. The device according to claim 1, wherein the base plate comprises a connector needle, the connector needle configured to penetrate a protective seal covering an entrance of a connector hub and a septum covering an entrance of a reservoir of the delivery part.

23. The device according to claim 22, wherein the protective seal comprises a deformable bubble-shaped membrane.

24. The device according to claim 23, wherein the reservoir and the deformable membrane are configured to be pushed together so that the deformable membrane is deformed and the connector needle penetrates the membrane and forms a fluid connection.

* * * * *